(12) United States Patent  
Gilbert

(10) Patent No.: US 8,998,881 B2
(45) Date of Patent: Apr. 7, 2015

(54) METHOD FOR DELIVERING DRUGS TO TISSUE UNDER MICROJET PROPULSION

(75) Inventor: Scott J. Gilbert, Menlo Park, CA (US)

(73) Assignee: Alza Corporation, Vacaville, CA (US)

( * ) Notice: Subject to any disclaimer, the term of this patent is extended or adjusted under 35 U.S.C. 154(b) by 2384 days.

(21) Appl. No.: 11/200,749

(22) Filed: Aug. 10, 2005

(65) Prior Publication Data

US 2007/0055214 A1    Mar. 8, 2007

(51) Int. Cl.
*A61M 31/00* (2006.01)
*A61M 5/30* (2006.01)
*A61M 5/20* (2006.01)
*A61M 5/315* (2006.01)
*A61M 5/19* (2006.01)

(52) U.S. Cl.
CPC ........... *A61M 5/30* (2013.01); *A61M 2205/587* (2013.01); *A61M 5/2046* (2013.01); *A61M 2205/59* (2013.01); *A61M 5/2053* (2013.01); *A61M 5/31511* (2013.01); *A61M 2210/0612* (2013.01); *A61M 5/19* (2013.01); *A61M 2210/0618* (2013.01); *A61M 5/3007* (2013.01)

(58) Field of Classification Search
CPC ... A61M 5/2053; A61M 5/30; A61M 5/3007; A61M 11/06; A61M 2210/0612
USPC .............. 604/68–72, 289, 290, 294–302, 521
See application file for complete search history.

(56) References Cited

U.S. PATENT DOCUMENTS

| | | |
|---|---|---|
| 2,752,918 A | 7/1956 | Uytenbogaar |
| 3,403,680 A | 10/1968 | Sinclair |
| 3,688,765 A | 9/1972 | Gasaway |
| 3,797,489 A | 3/1974 | Sarnoff |
| 3,802,430 A | 4/1974 | Schwebel et al. |
| 3,933,155 A | 1/1976 | Johnston |
| 3,945,379 A | 3/1976 | Pritz et al. |
| 4,031,889 A | 6/1977 | Pike |
| 4,089,334 A | 5/1978 | Schwebel et al. |
| D248,568 S | 7/1978 | Ismach |
| 4,108,176 A | 8/1978 | Walden |
| 4,137,804 A * | 2/1979 | Gerber et al. .................. 83/177 |
| 4,165,739 A | 8/1979 | Doherty et al. |
| 4,165,800 A | 8/1979 | Doherty et al. |
| 4,266,541 A | 5/1981 | Landau |
| 4,301,795 A | 11/1981 | Zimmermann |
| 4,342,310 A | 8/1982 | Lindmayer et al. |

(Continued)

FOREIGN PATENT DOCUMENTS

| | | |
|---|---|---|
| CN | 1147107 | 4/1997 |
| CN | 1361703 | 7/2002 |

(Continued)

OTHER PUBLICATIONS

"Drug." Merriam-Webster Online Dictionary. 2009. <http://www.merriam-webster.com/dictionary/drug>.*

(Continued)

*Primary Examiner* — Kami A Bosworth

(57) ABSTRACT

A method for delivering a drug into tissue includes the steps of: providing a drug delivery device having at least one nozzle and a drug contained in a portion of the device; identifying a site for delivery of the drug in or on tissue; placing a portion of the device on or near the site; and delivering the drug into the tissue at the site through at least one nozzle of the device under microjet propulsion.

8 Claims, 10 Drawing Sheets

(56) References Cited

U.S. PATENT DOCUMENTS

| | | | |
|---|---|---|---|
| 4,396,384 A | 8/1983 | Dettbarn et al. |
| 4,400,171 A | 8/1983 | Dettbarn et al. |
| 4,400,172 A | 8/1983 | Dettbarn et al. |
| 4,403,609 A | 9/1983 | Cohen |
| 4,403,986 A | 9/1983 | Dettbarn et al. |
| 4,421,508 A | 12/1983 | Cohen |
| 4,447,225 A | 5/1984 | Taff et al. |
| 4,518,384 A | 5/1985 | Tarello et al. |
| 4,518,385 A | 5/1985 | Lindmayer et al. |
| 4,560,377 A | 12/1985 | Geat et al. |
| 4,570,832 A | 2/1986 | Kroger |
| 4,596,556 A | 6/1986 | Morrow et al. |
| 4,623,332 A | 11/1986 | Lindmayer et al. |
| 4,626,242 A | 12/1986 | Fejes et al. |
| 4,678,461 A | 7/1987 | Mesa |
| 4,680,027 A | 7/1987 | Parsons et al. |
| 4,704,105 A | 11/1987 | Adojan et al. |
| 4,722,728 A | 2/1988 | Dixon |
| 4,722,729 A | 2/1988 | Dettbarn et al. |
| 4,790,824 A | 12/1988 | Morrow et al. |
| 4,850,967 A | 7/1989 | Cosmai |
| 4,874,367 A | 10/1989 | Edwards |
| 4,894,054 A | 1/1990 | Miskinyar |
| 4,913,699 A | 4/1990 | Parsons |
| 4,940,460 A | 7/1990 | Casey et al. |
| 4,941,880 A | 7/1990 | Burns |
| 4,944,726 A | 7/1990 | Hilal et al. |
| 5,009,637 A | 4/1991 | Newman et al. |
| 5,024,656 A | 6/1991 | Gassaway et al. |
| 5,026,343 A | 6/1991 | Holzer |
| 5,049,125 A | 9/1991 | Accaries et al. |
| 5,062,830 A | 11/1991 | Dunlap |
| 5,064,413 A | 11/1991 | McKinnon et al. |
| 5,073,165 A | 12/1991 | Edwards |
| 5,074,843 A | 12/1991 | Dalto et al. |
| 5,092,843 A | 3/1992 | Monroe et al. |
| 5,102,393 A | 4/1992 | Sarnoff et al. |
| 5,104,380 A | 4/1992 | Holman et al. |
| 5,151,098 A * | 9/1992 | Loertscher ............... 606/16 |
| 5,165,415 A | 11/1992 | Wallace et al. |
| 5,176,645 A | 1/1993 | Guerrero |
| 5,179,022 A | 1/1993 | Sanford et al. |
| 5,190,523 A | 3/1993 | Lindmayer |
| 5,256,142 A | 10/1993 | Colavecchio |
| 5,300,030 A | 4/1994 | Crossman et al. |
| 5,304,128 A | 4/1994 | Haber et al. |
| 5,307,953 A | 5/1994 | Regan |
| 5,312,335 A | 5/1994 | McKinnon et al. |
| 5,328,481 A | 7/1994 | Wang |
| 5,330,430 A | 7/1994 | Sullivan |
| 5,334,144 A | 8/1994 | Alchas et al. |
| 5,354,286 A | 10/1994 | Mesa et al. |
| 5,358,489 A | 10/1994 | Wyrick |
| 5,383,851 A | 1/1995 | McKinnon, Jr. et al. |
| 5,399,163 A | 3/1995 | Peterson et al. |
| 5,409,457 A * | 4/1995 | del Cerro et al. ............. 604/521 |
| 5,425,715 A | 6/1995 | Dalling et al. |
| 5,453,096 A | 9/1995 | Lataix |
| 5,480,381 A | 1/1996 | Weston |
| 5,499,972 A | 3/1996 | Parsons |
| 5,501,666 A | 3/1996 | Spielberg |
| 5,503,627 A | 4/1996 | McKinnon et al. |
| 5,503,628 A | 4/1996 | Fetters et al. |
| 5,520,639 A | 5/1996 | Peterson et al. |
| 5,527,287 A | 6/1996 | Miskinyar |
| 5,531,707 A | 7/1996 | Kers et al. |
| 5,540,657 A | 7/1996 | Kurjan et al. |
| 5,567,160 A | 10/1996 | Massino |
| 5,569,189 A | 10/1996 | Parsons |
| 5,569,190 A | 10/1996 | D'Antonio |
| 5,591,184 A * | 1/1997 | McDonnell et al. .......... 606/167 |
| 5,599,302 A | 2/1997 | Lilley et al. |
| 5,665,071 A | 9/1997 | Wyrick |
| 5,695,472 A | 12/1997 | Wyrick |
| 5,697,917 A | 12/1997 | Sadowski et al. |
| 5,704,911 A | 1/1998 | Parsons |
| 5,722,953 A | 3/1998 | Schiff et al. |
| 5,730,723 A | 3/1998 | Castellano et al. |
| 5,741,275 A | 4/1998 | Wyssmann |
| 5,746,714 A | 5/1998 | Salo et al. |
| 5,779,677 A | 7/1998 | Frezza |
| 5,782,802 A | 7/1998 | Landau |
| 5,792,089 A | 8/1998 | Penrose et al. |
| 5,792,099 A | 8/1998 | DeCamp et al. |
| 5,800,388 A | 9/1998 | Schiff et al. |
| 5,836,911 A | 11/1998 | Marzynski et al. |
| 5,840,061 A | 11/1998 | Mene et al. |
| 5,840,062 A | 11/1998 | Gumaste et al. |
| RE35,986 E | 12/1998 | Ritson et al. |
| 5,846,233 A | 12/1998 | Lilley et al. |
| 5,851,198 A | 12/1998 | Castellano et al. |
| 5,876,380 A | 3/1999 | Manganini et al. |
| 5,879,327 A | 3/1999 | DeFarges |
| 5,891,085 A | 4/1999 | Lilley et al. |
| 5,891,086 A | 4/1999 | Weston |
| 5,899,879 A | 5/1999 | Umbaugh |
| 5,899,880 A | 5/1999 | Bellhouse et al. |
| 5,899,888 A | 5/1999 | Jepson et al. |
| 5,911,703 A | 6/1999 | Slate et al. |
| 5,919,159 A | 7/1999 | Lilley et al. |
| 5,921,967 A | 7/1999 | Sadowski et al. |
| 5,938,637 A | 8/1999 | Austin et al. |
| 5,951,531 A | 9/1999 | Ferdman et al. |
| 5,957,886 A | 9/1999 | Weston |
| 5,957,897 A | 9/1999 | Jeffrey |
| 5,993,412 A | 11/1999 | Deily et al. |
| 6,010,478 A * | 1/2000 | Bellhouse et al. ............. 604/70 |
| 6,013,050 A | 1/2000 | Bellhouse et al. |
| 6,053,890 A | 4/2000 | Defarges et al. |
| 6,056,716 A | 5/2000 | D'Antonio et al. |
| 6,063,053 A | 5/2000 | Castellano et al. |
| 6,063,054 A | 5/2000 | Anderson et al. |
| 6,074,360 A | 6/2000 | Haar et al. |
| 6,080,130 A | 6/2000 | Castellano |
| 6,083,197 A | 7/2000 | Umbaugh |
| 6,096,002 A | 8/2000 | Landau |
| 6,099,504 A | 8/2000 | Gross et al. |
| 6,132,395 A | 10/2000 | Landau et al. |
| 6,135,979 A | 10/2000 | Weston |
| 6,149,626 A | 11/2000 | Bachynsky et al. |
| 6,156,008 A | 12/2000 | Castellano |
| 6,159,181 A | 12/2000 | Crossman et al. |
| 6,165,155 A | 12/2000 | Jacobsen et al. |
| 6,168,587 B1 | 1/2001 | Bellhouse et al. |
| 6,171,276 B1 | 1/2001 | Lippe et al. |
| 6,179,583 B1 | 1/2001 | Weston |
| 6,179,584 B1 | 1/2001 | Howitz et al. |
| 6,203,521 B1 | 3/2001 | Menne et al. |
| 6,210,359 B1 | 4/2001 | Patel et al. |
| 6,224,567 B1 | 5/2001 | Roser |
| 6,231,540 B1 | 5/2001 | Smedegaard |
| 6,232,113 B1 | 5/2001 | Lee |
| 6,251,099 B1 | 6/2001 | Kollias et al. |
| 6,258,063 B1 | 7/2001 | Haar et al. |
| 6,264,629 B1 | 7/2001 | Landau |
| 6,270,473 B1 | 8/2001 | Schwebel |
| 6,270,479 B1 | 8/2001 | Bergens et al. |
| 6,306,420 B1 | 10/2001 | Cheikh |
| 6,309,371 B1 | 10/2001 | Deboer et al. |
| 6,319,224 B1 | 11/2001 | Stout et al. |
| 6,344,027 B1 | 2/2002 | Goll |
| 6,361,991 B1 | 3/2002 | Furth et al. |
| 6,383,168 B1 | 5/2002 | Landau et al. |
| 6,387,078 B1 | 5/2002 | Gillespie, III |
| 6,406,455 B1 | 6/2002 | Willis et al. |
| 6,406,456 B1 | 6/2002 | Slate et al. |
| 6,425,879 B1 | 7/2002 | Egger et al. |
| 6,440,099 B2 | 8/2002 | Haar et al. |
| 6,440,105 B1 | 8/2002 | Menne |
| 6,447,482 B1 | 9/2002 | Rønborg et al. |
| 6,471,669 B2 | 10/2002 | Landau |
| 6,475,181 B1 | 11/2002 | Potter et al. |
| 6,506,177 B2 | 1/2003 | Landau |
| 6,554,202 B2 | 4/2003 | Ganan-Calvo |

(56) References Cited

U.S. PATENT DOCUMENTS

| | | |
|---|---|---|
| 6,558,348 B2 | 5/2003 | Parsons |
| 6,569,123 B2 | 5/2003 | Alchas et al. |
| 6,572,581 B1 | 6/2003 | Landau |
| 6,585,685 B2 | 7/2003 | Staylor et al. |
| 6,599,264 B1 | 7/2003 | Ernie et al. |
| 6,602,222 B1 | 8/2003 | Roser |
| 6,607,510 B2 | 8/2003 | Landau |
| 6,610,029 B2 | 8/2003 | Golan |
| 6,610,042 B2 | 8/2003 | Leon et al. |
| 6,613,010 B2 | 9/2003 | Castellano |
| 6,616,627 B2 | 9/2003 | Willis et al. |
| 6,620,135 B1 | 9/2003 | Weston et al. |
| 6,623,446 B1 | 9/2003 | Navelier et al. |
| 6,641,553 B1 | 11/2003 | Chee et al. |
| 6,641,554 B2 | 11/2003 | Landau |
| 6,645,169 B1 | 11/2003 | Slate et al. |
| 6,645,170 B2 | 11/2003 | Landau |
| 6,648,850 B2 | 11/2003 | Landau |
| 6,652,483 B2 | 11/2003 | Slate et al. |
| 6,673,034 B2 | 1/2004 | Castellano |
| 6,673,035 B1 | 1/2004 | Rice et al. |
| 6,673,038 B2 | 1/2004 | Weston |
| 6,676,630 B2 | 1/2004 | Landau et al. |
| 6,682,504 B2 | 1/2004 | Nelson et al. |
| 6,685,669 B2 | 2/2004 | Bellhouse et al. |
| 6,685,692 B2 | 2/2004 | Fathallah |
| 6,689,092 B2 | 2/2004 | Zierenberg et al. |
| 6,689,093 B2 | 2/2004 | Landau |
| 6,689,094 B2 | 2/2004 | Kollias et al. |
| 6,689,095 B1 | 2/2004 | Garitano et al. |
| 6,689,101 B2 | 2/2004 | Hjertman et al. |
| 6,716,190 B1 | 4/2004 | Glines et al. |
| 6,719,738 B2 | 4/2004 | Mehier |
| 6,740,062 B2 | 5/2004 | Hjertman |
| 6,746,429 B2 | 6/2004 | Sadowski et al. |
| 6,752,780 B2 | 6/2004 | Stout et al. |
| 6,752,781 B2 | 6/2004 | Landau et al. |
| 6,773,414 B2 | 8/2004 | Ljungquist |
| 6,783,509 B1 | 8/2004 | Landau et al. |
| 6,803,361 B2 | 10/2004 | Rijewijk et al. |
| 6,824,526 B2 | 11/2004 | Castellano |
| 6,835,187 B2 | 12/2004 | Alexandre et al. |
| 6,837,866 B1 | 1/2005 | Alexandre et al. |
| 6,849,060 B1 | 2/2005 | Brooks et al. |
| 6,881,200 B2 | 4/2005 | Bellhouse et al. |
| 6,905,475 B2 | 6/2005 | Hauschild et al. |
| 6,911,015 B2 | 6/2005 | Alexandre et al. |
| 6,913,592 B2 | 7/2005 | Parsons |
| 6,913,593 B1 | 7/2005 | Alexandre et al. |
| 6,939,323 B2 | 9/2005 | Angel et al. |
| 6,942,645 B2 | 9/2005 | Alexandre et al. |
| 6,981,961 B1 | 1/2006 | Navelier et al. |
| 7,011,649 B2 | 3/2006 | De La Serna et al. |
| 7,097,634 B2 | 8/2006 | Gilbert |
| 7,381,201 B2 | 6/2008 | Gilbert et al. |
| 7,654,983 B2 | 2/2010 | De La Serna et al. |
| 2001/0005781 A1 | 6/2001 | Bergens et al. |
| 2002/0007143 A1* | 1/2002 | Gordon ............ 604/70 |
| 2002/0035348 A1 | 3/2002 | Hjertman |
| 2002/0099329 A1 | 7/2002 | Castellano |
| 2003/0014006 A1 | 1/2003 | Alexandre et al. |
| 2003/0078551 A1* | 4/2003 | Hochrainer et al. ...... 604/295 |
| 2004/0249339 A1 | 12/2004 | Willis et al. |
| 2005/0154350 A1 | 7/2005 | Willis et al. |
| 2007/0052139 A1 | 3/2007 | Gilbert |
| 2007/0055199 A1 | 3/2007 | Gilbert |
| 2007/0055200 A1 | 3/2007 | Gilbert |
| 2007/0055214 A1 | 3/2007 | Gilbert |
| 2008/0161742 A1* | 7/2008 | Domb et al. ............ 604/20 |

FOREIGN PATENT DOCUMENTS

| | | |
|---|---|---|
| DE | 19712064 A1 | 10/1998 |
| EP | 29591 A1 | 6/1981 |
| EP | 29591 B1 | 9/1982 |
| EP | 295917 A2 | 12/1988 |
| EP | 295917 A3 | 3/1989 |
| EP | 897728 A1 | 2/1999 |
| EP | 982518 A2 | 3/2000 |
| EP | 982518 A3 | 11/2000 |
| EP | 897728 B1 | 5/2003 |
| EP | 1443992 A2 | 8/2004 |
| EP | 982518 B1 | 3/2005 |
| EP | 1443992 B1 | 1/2007 |
| EP | 1752174 A1 | 2/2007 |
| EP | 1752176 A1 | 2/2007 |
| FR | 2690838 A1 | 11/1993 |
| FR | 2805749 A1 | 9/2001 |
| GB | 1284312 A | 8/1972 |
| HU | 179577 | 11/1982 |
| HU | 186718 | 9/1985 |
| HU | 197218 | 2/1988 |
| HU | 194056 | 11/1988 |
| HU | 195428 | 11/1988 |
| HU | 189198 | 6/1990 |
| HU | 211712 | 12/1995 |
| HU | 214350 | 3/1998 |
| HU | 218191 B | 6/2000 |
| JP | 62240038 A | 10/1987 |
| JP | 1017654 A | 1/1989 |
| JP | 3222962 A | 10/1991 |
| JP | 2001511404 A | 8/2001 |
| KR | 10-1999-0087354 A | 12/1999 |
| WO | WO 8800843 | 2/1988 |
| WO | WO 9413342 A1 | 6/1994 |
| WO | WO 9516481 | 6/1995 |
| WO | WO 9527523 A1 | 10/1995 |
| WO | WO 9529720 A1 | 11/1995 |
| WO | WO 9531235 A1 | 11/1995 |
| WO | WO 9737705 A1 | 10/1997 |
| WO | WO 9800188 A1 | 1/1998 |
| WO | WO 9812121 A1 | 3/1998 |
| WO | WO 9817332 A2 | 4/1998 |
| WO | WO 9817332 A3 | 6/1998 |
| WO | WO 9842959 | 10/1998 |
| WO | WO 9906100 A2 | 2/1999 |
| WO | WO 9906100 A3 | 4/1999 |
| WO | WO 0029050 A1 | 5/2000 |
| WO | WO 00/35520 A1 | 6/2000 |
| WO | WO 0035520 A1 | 6/2000 |
| WO | WO 0050107 A1 | 8/2000 |
| WO | WO 0071185 A2 | 11/2000 |
| WO | WO 0035520 A9 | 12/2000 |
| WO | WO 0072908 A1 | 12/2000 |
| WO | WO 0117593 A1 | 3/2001 |
| WO | WO 0071185 A3 | 4/2001 |
| WO | WO 01/41656 A | 6/2001 |
| WO | WO 0141656 A1 | 6/2001 |
| WO | WO 0164269 A1 | 9/2001 |
| WO | 01/78810 A1 | 10/2001 |
| WO | WO 2004004810 A1 | 1/2004 |
| WO | 2004/093818 A2 | 11/2004 |

OTHER PUBLICATIONS

EP Search Report for Application EP 06 25 4198 Date of Completion Oct. 19, 2006.

Canadian Office Action for Application No. 2,555,931 dated Mar. 22, 2013.

Final Notice of Preliminary Rejection issued by the Korean Patent Office dated May 27, 2013 for Application No. 10-2006-0075157.

Notice of Preliminary Rejection dated Oct. 23, 2012 issued by the Korean Patent Office for corresponding Application No. 10-2006-0075157.

* cited by examiner

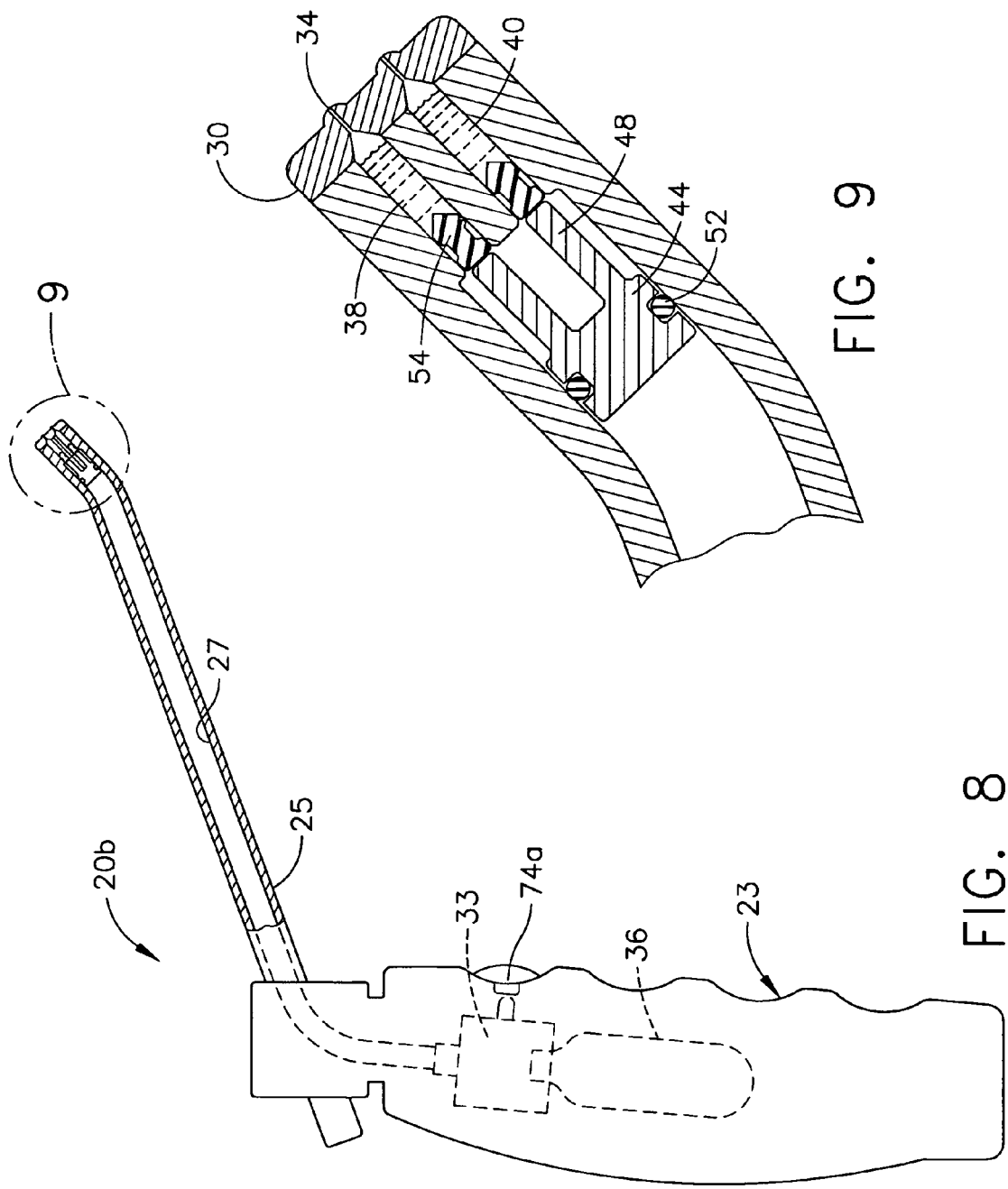

METHOD FOR DELIVERING DRUGS TO TISSUE UNDER MICROJET PROPULSION

FIELD AND BACKGROUND OF THE INVENTION

The present invention relates, in general, to drug delivery and, in particular, to a new and useful device and method for the needle-free delivery of drugs with minimal trauma to tissue and that are suitable for delivering drugs in sensitive areas of the body such as the eye, nasal passageways, mouth and other areas of the body.

Despite the continual advances in medical technology, particularly in the treatment of various diseases such as heart disease, vascular disease, ophthalmic disease, cancer, pain, allergies, orthopedic repair and many other diseases and conditions, there are a significant number of patients for whom conventional surgical and interventional therapies are not feasible or are insufficient to treat the disease or condition. For many patients, medical treatment with drugs and the like is the only feasible treatment available.

There have been many recent advances in drug therapies, particularly with regard to cell or site-specific therapeutics also known as "local" drug delivery. Unlike the systemic administration of therapeutics, typically taken orally or given intravenously, much of the effectiveness of local drug delivery or cell or site-specific therapeutics is based on the ability to accurately and precisely deliver the therapeutics to the targeted site within the body.

Needle injection devices are the most commonly used means for the local delivery or site-specific administration of agents or solutions. Although there have been advances in needle-based drug delivery/injection systems, these systems have significant shortcomings and disadvantages. One such disadvantage is that the use of a needle or other penetrating means to inject the targeted tissue area unavoidably involves making a hole into the target site thereby causing trauma and tissue injury at the local tissue site.

Another disadvantage with this needle penetrating and injection approach is that it is very common for a substantial amount of the injectate to leak back out or exude from the hole created by the needle or penetrating member. Often, this leaked injectate is released systemically throughout the body or is wasted depriving the patient of the prescribed therapy or dosing amounts of the drug. This also results in increased treatment costs and requires more injections, time and agent in order to achieve the desired affect.

Furthermore, it is known that needle injections or penetration into the tissue can traumatize or destroy tissue cells and, as a result, increase a patient's risk of post-operative trauma, pain and discomfort at the local site and surrounding area. This is particularly due to the difficulty in precisely controlling the penetration of the needle during injection. The more injections or penetrations, the greater the cell destruction and tissue trauma that is likely experienced. Still another disadvantage of needle-based injections, especially where multiple injections are required, is the inability to carefully track the location of each injection site so as to prevent the accidental delivery of drug to non-diseased tissue or repeat delivery of the drug to the same injection hole.

Other known drug delivery devices and methods do not involve needle-based drug delivery. Instead, devices such as indwelling catheters are used for releasing the therapeutic agent in a steady, controlled-release fashion. These types of devices could present a greater risk of releasing the agent systemically. Additionally, with these types of devices, it is more difficult to assess the actual dosing of the target area that takes place. Thus, these types of devices have the disadvantages of being less effective, possibly not as safe, and definitely more costly than the commonly known needle injection approaches and technology.

Another condition in which site-specific or local drug delivery is commonly employed is in the treatment of peripheral vascular disease (such as deep vein thrombosis and embolisms). One such treatment is venous lytic therapy, the dissolving of blood clots (thrombus) in the peripheral vasculature (e.g., femoral and iliac arteries and veins). Lytic therapy involves systemically infusing thrombolytics, such as urokinase, streptokinase, reteplase and tPA. Other more recently developed procedures involve directly delivering the thrombolytics into the thrombus site through the use of indwelling infusion catheters. In order to effectively lyse the thrombus, the thrombolytics are typically infused for many hours, even as much as a day or more, increasing the necessary length of hospital stay and the overall cost of the procedure.

One common approach for eliminating a needle in local drug delivery is to use conventional needle-free jet injectors. Needle-free jet injection technology was introduced nearly 40 years ago for use in mass immunization campaigns. Today, more than fifteen companies develop and manufacture jet injectors for the intradermal and transdermal (subcutaneous and intramuscular) delivery of drugs. And while these modern designs offer tremendous improvements in size, cost and convenience over their predecessors, the fundamental functionality has remained unchanged. Principally, compressed gas is used to drive a medicament (either liquid or dry powder) through a single orifice at moderately high speed, allowing the medicament to be deposited in or beneath the skin by piercing through it. One example of a known needle-free jet injector is disclosed in WO 00/35520 and U.S. Pat. No. 6,406,455 B1 (Willis et al.—assigned to BioValve Technologies, Inc.).

Further, needle-free jet injection has long been touted as a painless procedure, but clinical studies comparing jet injecting devices to a conventional needle and syringe have shown pain scores to be equivalent to that of a 25 ga. needle. In great part, this is due to the size of the injection stream and, thus, the size of the nozzle orifice. Existing devices all use a nozzle orifice of about 0.006" to 0.008" in diameter. These conventional needle-free jet injectors are known to incorporate only a single injection chamber and inject the entire drug content through a single plastic nozzle having a typical orifice diameter of 0.006"-0.008" or 150-200 microns (0.15 mm-0.2 mm). These jet injectors typically deliver volumes ranging from 0.100 cc (100 micro liters) to 0.500 cc (500 micro liters), and even as much as 1 cc (1,000 micro liters). There are several significant limitations with current jet injection technology. First, injection times associated with these conventional needle-free jet injectors are typically several seconds in length, which puts the patient at risk of laceration if they should move (e.g., flinch) or if the injector should be jarred from the injection site during an injection. Second, the perceived pain is equivalent to a conventional needle and syringe. This has perhaps been the greatest single reason why jet injection has not been more widely accepted. Third, jet injectors are prone to deliver so-called "wet injections" where medicine leaks back out through the site of injection, a result that has given rise to concerns about accuracy of the delivered dose.

The first two items, pain and wet injections, are the result of the nozzle orifice size (approximately 0.006" in current jet injectors). This size resulted more from the practical limitations of plastic injection molding for high volume commercial manufacturing than from any effort at optimizing the size for user comfort and minimization or elimination of any "leaking" of the injected medicament. This trade-off of suboptimal performance for manufacturability has resulted in a marginalized product that has not enjoyed the market acceptance it otherwise might have.

One particular type of conventional needle free jet is described in U.S. Pat. No. 6,716,190 B1 (Glines et al.) which teaches a device and methods for the delivery and injection of therapeutic and diagnostic agents to a target site within a body. This device and method uses a complex system comprising a nozzle assembly having an ampule body and channels milled or machined within the distal surface of the ampule body. These channels operate as a manifold and are arranged orthogonal to a reservoir orifice. The reservoir orifice ejects or expels the contents contained within the ampule body to the orthogonally arranged channels which channel the contents to a plurality of dispersion orifices orthogonally arranged to the channels. The dispersion orifices are orthogonal to the channels and located within the generally planar distal target-facing surface. Not only is this particular arrangement complex, but it requires high delivery pressures for the contents in the ampule in a range from about 1800 to 5000 psi, with some applications in a range from about 1800 to 2300 psi. Additionally, the dispersion orifices have a diameter of from about 0.1 mm to about 0.3 mm (100 to 300 microns). Even though such a device does not use a needle, the negative outcome involved with using such a device and arrangement is that it is likely to cause excessive trauma to the tissue at the delivery site as well as cause unwanted and unnecessary pain and/or discomfort to the end user or patient due to the required high delivery pressures as well as the relatively large size of the dispersion orifices. Accordingly, the Glines et al. device and method are not suitable for microjet delivery of drugs especially in sensitive areas of the body such as the eye, nasal passageways and mouth or other sensitive areas of the body especially those areas that are easily prone to trauma, pain and discomfort.

Accordingly, there are a number of sensitive areas in the body and disease states that are extremely difficult to treat using local drug delivery. For example, there are a myriad of ophthalmic diseases that are difficult to treat and delivery of the drug to the site of disease, i.e. the eye, is often painful or psychologically uncomfortable for the patient. Relevant examples of these diseases that are extremely difficult to treat include age-related macular degeneration (AMD), diabetic retinopathy, choroidal neovascularization (CNV), macular edema, uveitis, and the like.

For these types of disease, systemic administration of drug commonly yields subtherapeutic drug concentrations in the eye and may have significant adverse effects. Consequently, current treatment for diseases of the eye often involves direct injection of the medicament into the eye via a conventional needle and syringe—a painful and undesirable means of delivery for the patient. Further, chronic treatment requires repeated injections that can result in plaque formations and scarring in the eye, retinal detachment, and endophthalmitis.

As a result of these complications, alternative means of drug delivery to the eye are being developed. Research areas for delivery include iontophoresis, drug-eluding ocular implants, photodynamic therapy, "sticky" eye drops, and the like. And, it is well established that each of these approaches has its own limitations.

For instance, iontophoresis has a practical limit to the size of the drug molecule being delivered. It could not, for instance, be expected to deliver molecules with a molecular weight above 20,000 Daltons. Yet, many new compounds, especially some promising proteins, are well above this size, ranging to as large as 150,000 Daltons.

Additionally, ocular implants require a surgical procedure for implantation and explantation—procedures that are costly, painful, and can result in scarring to the eye. Implants have the further limitation of physical size and the amount of drug that can be loaded or put on board the implant.

It is also known that photodynamic therapy is an unproven technology whose long-term effects are not understood and may well be harmful to the retina. Alternatively, eye drops have long been considered the most convenient (and therefore perceived to be more acceptable) means of delivery of drugs to the eye. Eye drops, however, are very quickly washed out of the eye and afford only minimal delivery of the contained drug.

As a result, "sticky" eye drops, that is eye drops which provide mucosal adhesion, have been developed to prevent the "wash-out" effect. But, the rapidity of the cellular turnover at the surface of the eye is believed to be limiting in the effectiveness of this means of delivery. Further, the mechanism of delivery from eye drops is passive diffusion across the sclera. And, passive diffusion cannot deliver drugs with a molecular weight greater than about 500 Daltons. Still further, the delivery is systemic rather than targeted to the eye itself.

Consequently, there are currently no truly acceptable means of delivering active therapeutic agents to the eye and other sensitive areas of the body, especially the emerging macromolecules that are showing promise in the treatment of a variety of ophthalmic diseases and diseases associated with these other sensitive areas of the body.

To date, there have been no known devices or methods that provide for true needle-free delivery of drugs regardless of size of the drug molecules involved as well as provide for true needle-free delivery of drugs with minimal trauma to tissue and that are suitable for delivering drugs in sensitive areas of the body such as the eye, nasal passageways or mouth.

To date, there have also been no known devices that provide for the true needle-free delivery of drugs wherein the devices are microjet delivery devices that are simple and efficient in design and construction, low cost and easy to manufacture.

SUMMARY OF THE INVENTION

The present invention is directed to new and useful devices and methods for the needle-free delivery of drugs with minimal trauma to tissue and that are suitable for delivering drugs in sensitive areas of the body such as the eye, nasal passageways, mouth and other areas of the body.

Thus, the present invention is directed to a device for delivering a drug comprising:
  a housing;
  at least one nozzle at a portion of the housing;
  a source of drug in the housing;
an energy source for providing a driving pressure of from about 800 to about 2,000 psi for driving the drug through the at least one nozzle and out of the housing.

Additionally, the drug is driven through the at least one nozzle within a time ranging from about 10 msec to about 200 msec upon activation of the energy source. Moreover, the at least one injection nozzle has a diameter ranging between about 10 μm to about 50 μm.

Furthermore, the present invention is also directed to a device for delivering a drug comprising:
  a delivery tube, the delivery tube having a pressure chamber therein;

at least one nozzle at a distal end of the delivery tube and in fluid communication with the pressure chamber;

a source of drug adjacent the at least one nozzle;

a handle at a proximal end of the delivery tube; and an energy source in the handle for providing a driving pressure from about 800 to about 2,000 psi for driving the drug through the at least one nozzle and out of the delivery tube.

Additionally, the present invention is also directed to a method for making a jet injection drug delivery device, wherein the drug delivery device has at least one drug reservoir and at least one injection nozzle, wherein the method comprises the steps of:

identifying a drug desired to be delivered;

identifying a volume of the drug desired to be delivered;

establishing a reservoir diameter for the at least one drug reservoir;

establishing a nozzle diameter for the at least one injection nozzle;

identifying a tissue model for delivery of the drug;

identifying a penetration depth in the tissue model for the delivery of the drug; and injecting the drug into the tissue model under variable pressure until the desired penetration depth is achieved.

Moreover, the method further comprises identifying an optimal pressure range for the drug delivery device that achieves the desired penetration depth. An optimal pressure range for the device according to the present invention is from about 800 to about 2,000 psi and an optimal pressure range at a tip of the at least one injection nozzle for the device of the present invention is from about 4,000 to about 25,000 psi.

The present invention is also directed to a method for delivering a drug into tissue comprising the steps of:

providing a drug delivery device having at least one nozzle and a drug contained in a portion of the device;

identifying a site for delivery of the drug in or on tissue;

placing a portion of the device on or near the site; and delivering the drug into the tissue at the site through at least one nozzle of the device under microjet propulsion at a driving pressure from about 800 to about 2,000 psi.

The method further comprises delivering the drug into the tissue at the site with a pressure at a tip of the at least one nozzle ranging up to about 4,000 to about 25,000 psi.

BRIEF DESCRIPTION OF THE DRAWINGS

The novel features of the invention are set forth with particularity in the appended claims. The invention itself, however, both as to organization and methods of operation, together with further objects and advantages thereof, may be understood by reference to the following description, taken in conjunction with the accompanying drawings in which:

FIG. 8 is side view in partial cross-section of another embodiment of a microjet drug delivery device particularly useful for applications such as nasal use in accordance with the present invention;

FIG. 9 is a partial, enlarged side view of the distal end of the device of FIG. 8 in accordance with the present invention;

DESCRIPTION OF THE PREFERRED EMBODIMENTS

Figure 1:
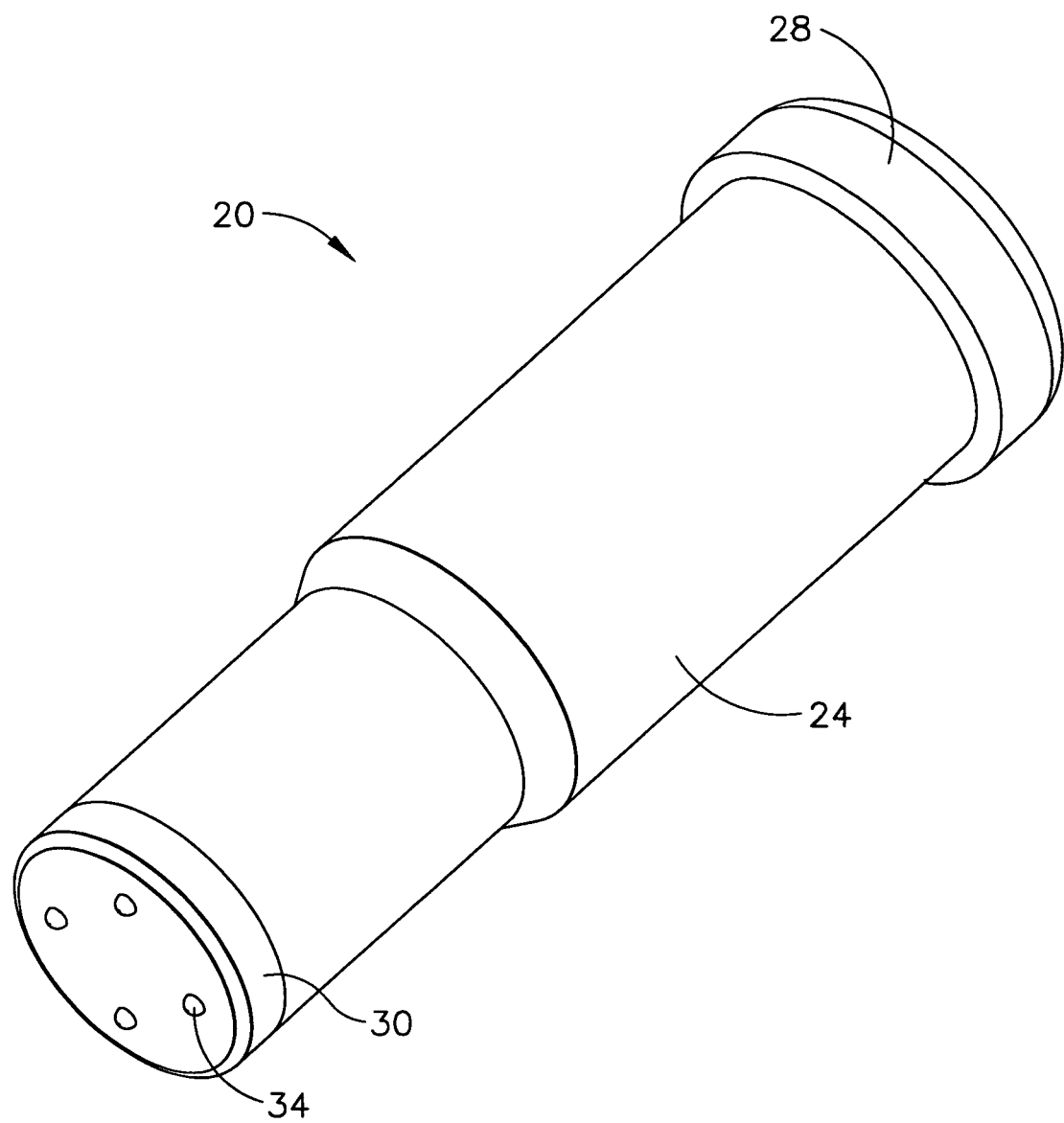
FIG. 1 is a perspective view of one embodiment of a microjet drug delivery device in accordance with the present invention.

The present invention is directed to novel drug delivery devices, their methods of manufacture and their methods of use. As best shown in FIGS. 1-10, the present invention is a needle-free (needle-less) microjet drug delivery device 20, 20*a* and 20*b*, their methods of manufacture and their methods of use which are all elaborated in greater detail below. The drug delivery device 20, 20*a* and 20*b*, in accordance with the present invention is a needle-free jet injection device that delivers drugs, such as liquid drug formulations, to a patient by injecting very fine streams of the drug formulations at high velocity. Drug delivery device 20, 20*a* and 20*b* provides for a less painful means of administering drugs than a conventional needle and syringe devices as well as known needle-less injection devices. Drug delivery device 20, 20*a* and 20*b*, in accordance with the present invention, can be used in a variety of medical applications, including transdermal, dermal, intraocular, intranasal, oral, and, generally, transmucosal drug delivery.

The terms "drug delivery device", "delivery device", "needle-free drug delivery device", "needle-free microjet drug delivery device", "microjet drug delivery device", "needle-less drug delivery device", "needle-less microjet drug delivery device", "needle-free jet injection device", "needle-less jet injection device", "jet injection device", "microjet device" and "microjet" including various combinations of any parts of these terms, are all intended to have the same meaning and are used interchangeably herein.

The terms "active agent formulation" and "drug formulation" and "formulation" intends the drug or active agent optionally in combination with pharmaceutically acceptable carriers and additional inert ingredients. The formulation can be either in solid, liquid or semi-solid or semi-liquid or combinations thereof.

The terms "drug", "agent", active agent" and "pharmaceutical composition" are used interchangeably herein and refer to an agent, drug, compound, composition of matter or mixture thereof, including its formulation, which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of drugs or agents useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, human pancreas hormone releasing factor, antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)I-$I_b III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, growth factor signal transduction kinase inhibitors, chemical compound, biological molecule, nucleic acids such as DNA and RNA, amino acids, peptide, protein or combinations thereof.

It is to be understood that more than one drug or agent may be combined or mixed together and incorporated into or used by the present invention, and that the use of the term "drug", "agent"" or "drug" or "pharmaceutical composition" in no way excludes the use of two or more such drugs, agents, active agents and or pharmaceutical compositions.

One embodiment of the drug delivery device 20 in accordance with the present invention is illustrated in FIGS. 1-4. The drug delivery device 20 is a needle-free jet injection device especially useful for injecting drug delivered under microjet propulsion in very fine streams at high velocity into various types of body tissue, to include organs. By way of example, the drug delivery device 20 in accordance with the present invention is particularly useful for the dermal or transdermal delivery of drugs to a patient, i.e. as a dermal or transdermal drug delivery device for delivering drugs without a needle to the various layers of skin or through the layers of skin and into the patient's blood stream and circulatory system. Although, the drug delivery device 20, in accordance with the present invention, is not limited to dermal and transdermal applications, but rather, is intended to be used for other types of tissue and other medical, therapeutic and diagnostic applications.

Figure 2:
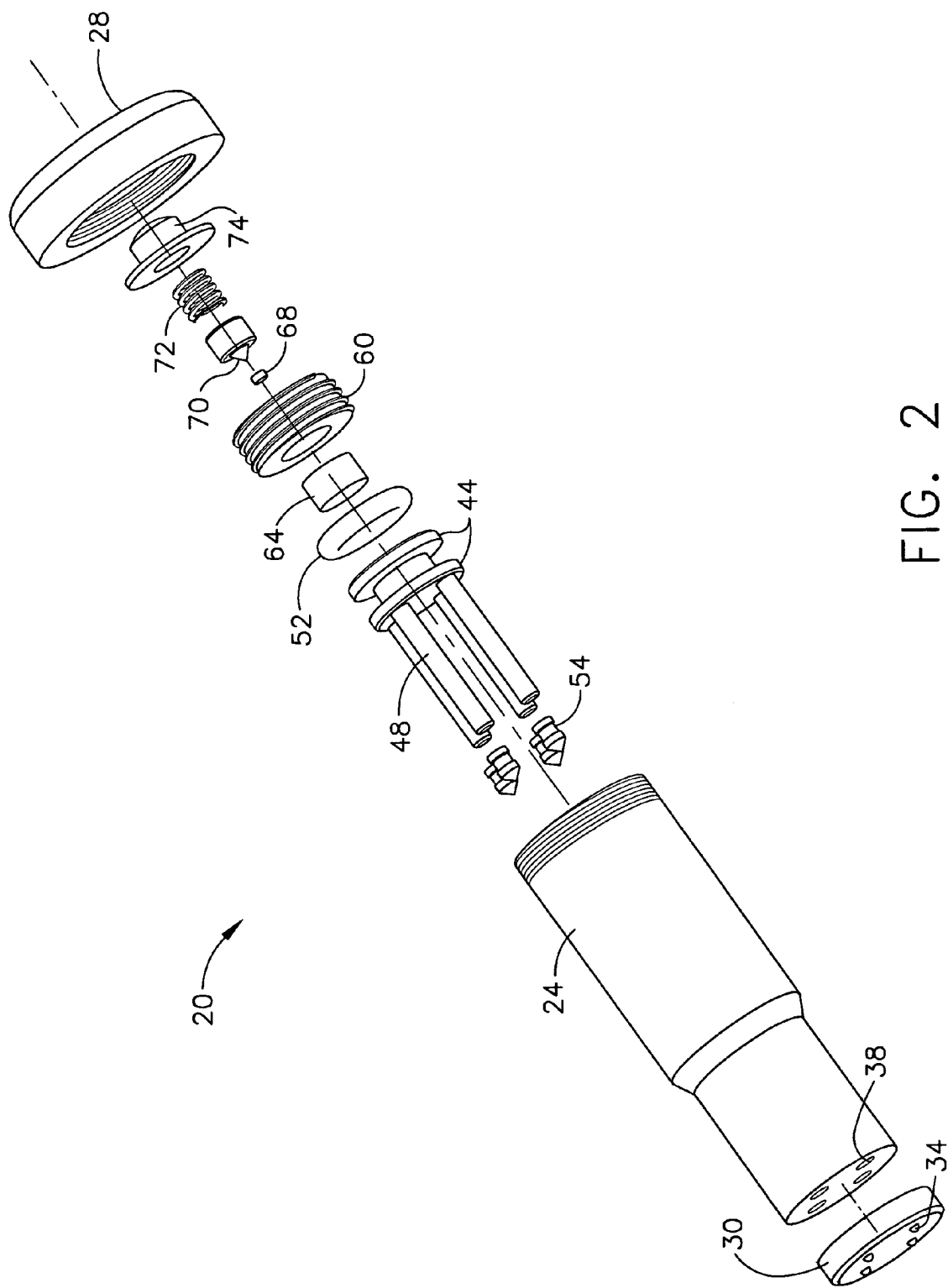
FIG. 2 is an exploded view of the device of FIG. 1 in accordance with the present invention.
Figure 3:
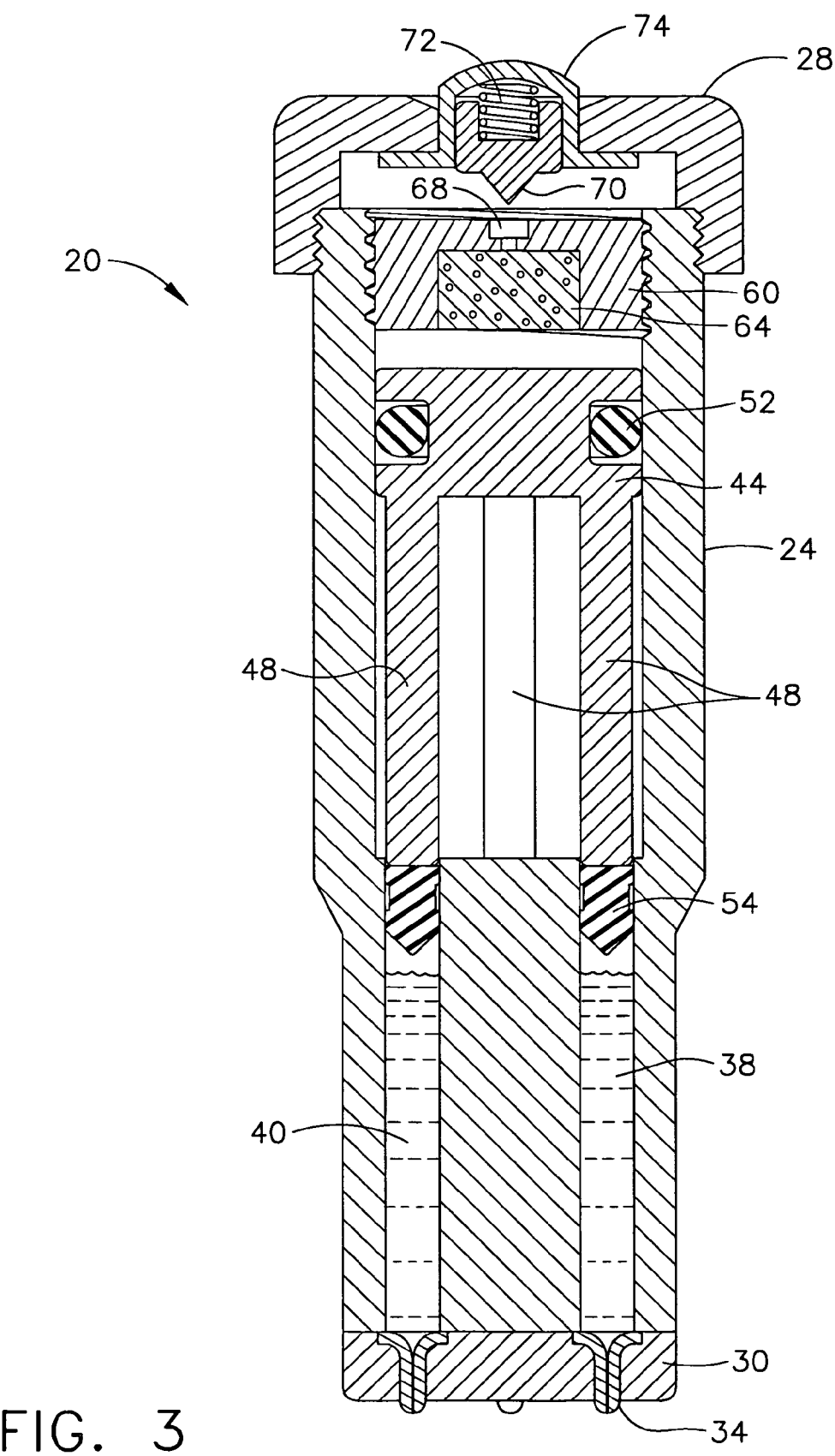
FIG. 3 is a view in cross-section of the device of FIG. 1 in a pre-fired configuration in accordance with the present invention.
Figure 4:
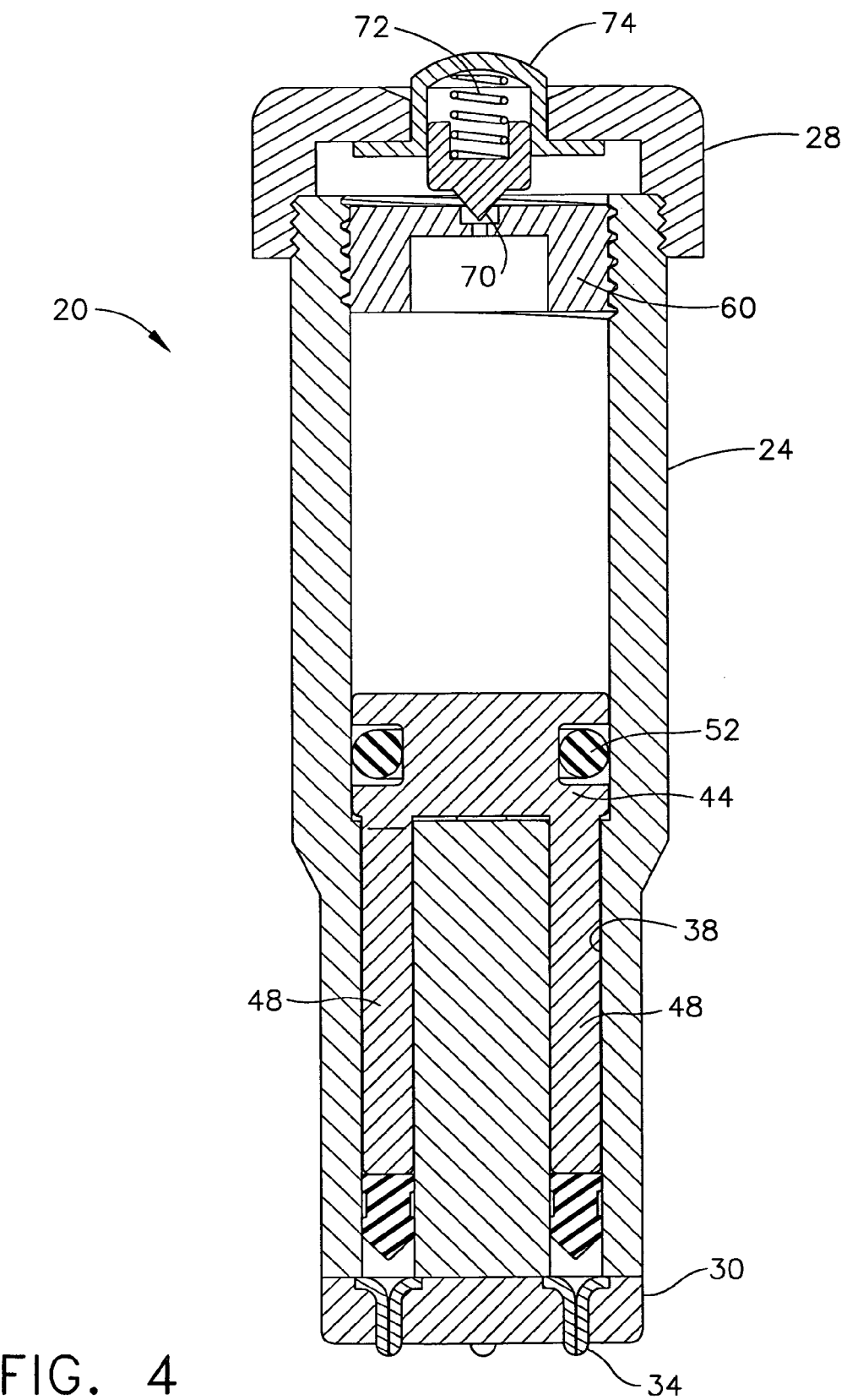
FIG. 4 is a view in cross-section of the device of FIG. 1 in a fired configuration in accordance with the present invention.

The drug delivery device 20 has a housing 24 and a cap 28 at a proximal end of the housing 24 and a nozzle plate 30 at the distal end of the housing 24. One or more nozzles 34 or a plurality of nozzles 34, which are jet injection nozzles (also referred to as "micro-nozzles"), are arranged in the nozzle plate 30. As shown in FIGS. 1-4, injection nozzles 34 terminate as small outward protrusions from the outer surface of nozzle plate 30 thereby providing the user with tactile feedback for the proper positioning and alignment of the injection nozzles 34 on the surface of the user's body tissue. As best illustrated in FIGS. 2, 3 and 4, housing 24 further includes one or more reservoirs 38 aligned with and in fluid communication with the one or more nozzles 34. Each reservoir 38 is longitudinally arranged in the housing 24 and serves as a drug reservoir or storage space for drug 40.

Each reservoir is shaped to receive a pushrod 48 and a reservoir seal 54 attached or fixed to the distal end of each pushrod 48. Pushrod 48 and reservoir seal 54 are in direct longitudinal alignment with each reservoir 38 and pushrod 48 and reservoir seal are movably located (longitudinally movable) within each drug reservoir 38. Each reservoir seal 54 is designed to prevent drug 40 from leaching or leaking from the drug reservoir 38. Thus, reservoir seal 54 is in movable sealable contact with the inner wall of the drug reservoir 38.

The pushrod 48 and reservoir seal 54 are slidably movable longitudinally in each reservoir 38. Piston 44 is integral to or fixed to the proximal end of each pushrod 48 and serves as a driving platform for accumulating and exerting a driving force to the pushrods 48. Piston 44 can be fixed as a single unit to the proximal end of all pushrods 48 in order to operate and move each pushrod 48 simultaneously within each reservoir 38 or piston 44 can be fixed to the proximal end of each pushrod 48 individually in order to selectively and individually operate and move each pushrod 48 within reservoir 38.

In this example, piston 44 has a cylindrical shape shaped to fit securely within and in moveable engagement with inner wall of housing 24 that is also of a cylindrical shape. Piston 44 has a circumferential space shaped to receive an O-ring seal 52 that is also shaped to fit securely within and in moveable engagement with inner wall of housing 24 along with piston 44. Seal 52 can be any type of seal so long as it prevents gas, discharge contents, or other matter from leaking or penetrating past piston 44.

As best shown in FIG. 3 (drug delivery device 20 loaded with drug 40 and in its pre-fired configuration), an energy source for discharging a driving force to the piston 44 is located proximal or superior to the piston 44 within housing 24, for instance, in one embodiment according to the present invention, a charge housing 60 located in the proximal or superior portion of the housing 24. Pyrotechnic charge 64 is contained within charge housing 60. A primer 68 is located adjacent pyrotechnic charge 64 for holding a small explosive charge that delivers pyrotechnic energy or ignition energy to the pyrotechnic charge 64 for igniting the pyrotechnic charge 64 upon activation of primer 68.

A striker pin 70 is located in cap 28 and moveably engages or moveably contacts primer 68 for activating primer 68 and initiating the explosive charge contained in primer 68. Striker pin 70 is moveably connected to an activation element such as an activation button 74 that is movably biased by spring 72. Thus, activation button is movably biased to striker pin 70 within cap 28 for driving striker pin 70 into the primer 70 upon a sufficient downward force pressed upon activation button 74, for instance, by the thumb of the user or patient.

As best shown in FIG. 4 (drug delivery device 20 in its fired configuration after having injected drug 40 under microjet propulsion), upon depressing the activation button 74, striker pin 70 strikes primer 68 thereby activating primer 68, which, in turn, cause the extremely rapid combustion of a pyrotechnic charge 64. This controlled explosion provides the driving force necessary to slidably advance the piston 44 and the affixed pushrods 48 through the reservoirs 38 causing the pushrods 48 to expel by microjet propulsion the drug 40 out through the injection nozzles 34.

The energy source, such as pyrotechnic charge 64 or compressed gas 36 (FIGS. 8 and 10) delivers sufficient energy and driving pressure to main drive piston 44 and associated pushrods 48 that ranges from about 800 to about 2,000 psi. In turn, the energy and pressure at the tips of micronozzles 34 ranges from about 4,000 to about 25,000 psi at each microzzle tip, and preferably at a range from about 8,000 to about 12,000 psi at each microzzle tip, and more preferably at about 10,000 psi at each microzzle tip.

Figure 5:
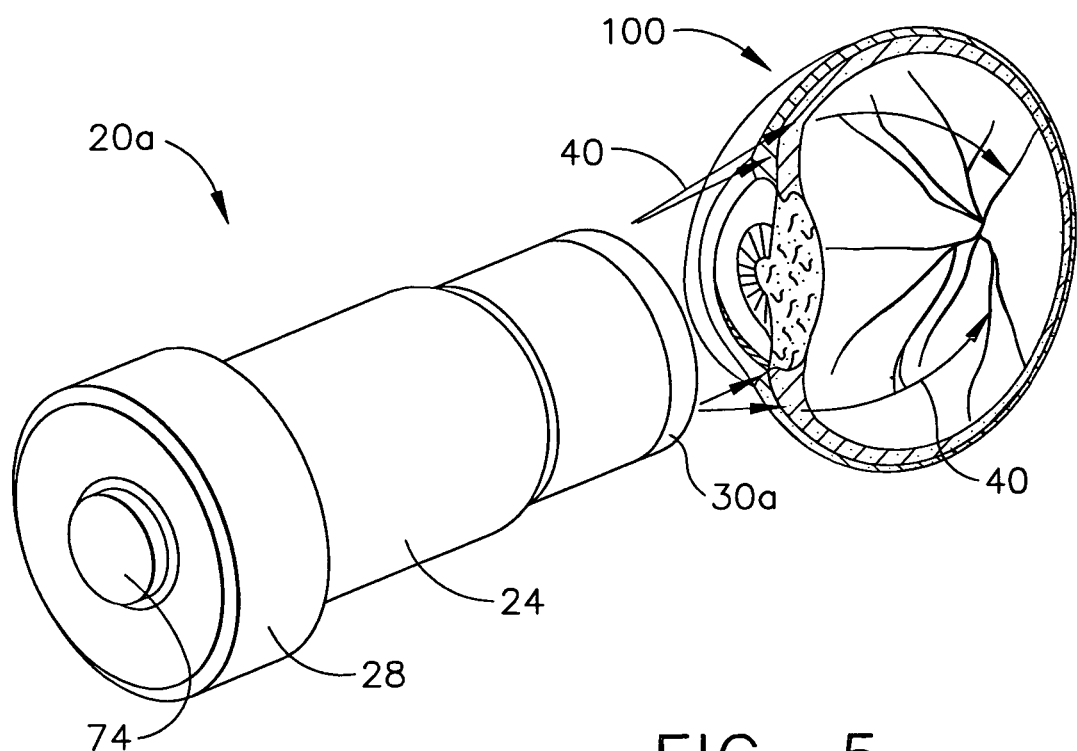
FIG. 5 is a proximal, perspective view of another embodiment of a microjet drug delivery device particularly useful for applications such as ocular use in accordance with the present invention.
Figure 6:
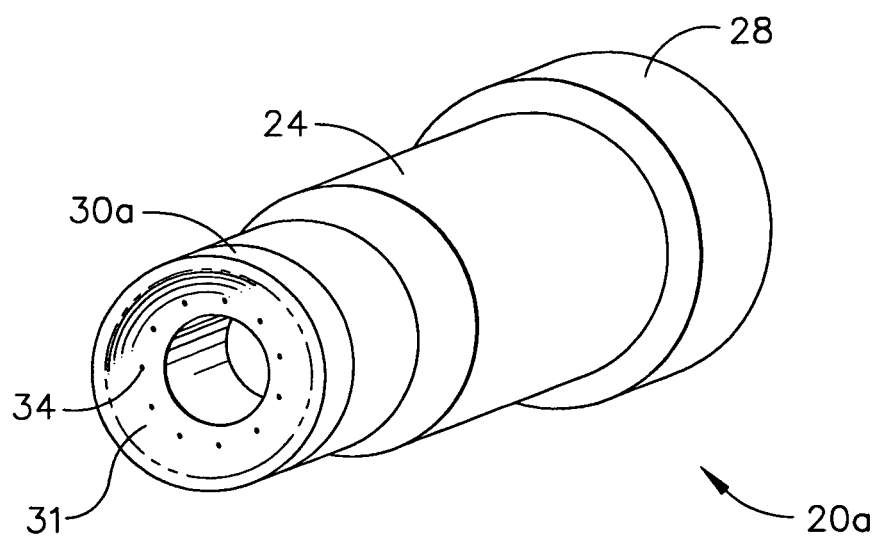
FIG. 6 is distal, perspective view of the device of FIG. 5 in accordance with the present invention.

For all embodiments of the present invention, the same reference numerals are used to designate the same or similar features and parts. Accordingly, FIGS. 5, 6, 7A and 7B, illustrate another embodiment of the present invention that is particularly useful for ophthalmic and ocular applications such as delivering drug 40 a patient eye 100. Thus, nozzle plate 30a at distal end of housing 24 has a contoured distal end 31 that is a concave ring having an opening in a center portion thereof. In this example, contoured distal end 31 has a plurality of injection nozzles 34 circumferentially arranged within the contour (concave region) defined by the contoured distal end 31 and spaced proximally a distance away from the outer surface edge of the outer circumference (periphery or outer edge) of contoured distal end 31. Accordingly, in this example, nozzle plate 30a having contoured distal end 31 is shaped to receive a patient's eye 100 wherein the pupil of the eye 100 can be situated within the center portion (open space) of the circumferential ring of the contoured distal end 31. Thus, if desired, drug 40 can be delivered under microjet propulsion to areas of the eye 100 outside the pupil, such as the vitreous or sclera, as best shown in FIG. 5.

Figure 7A:
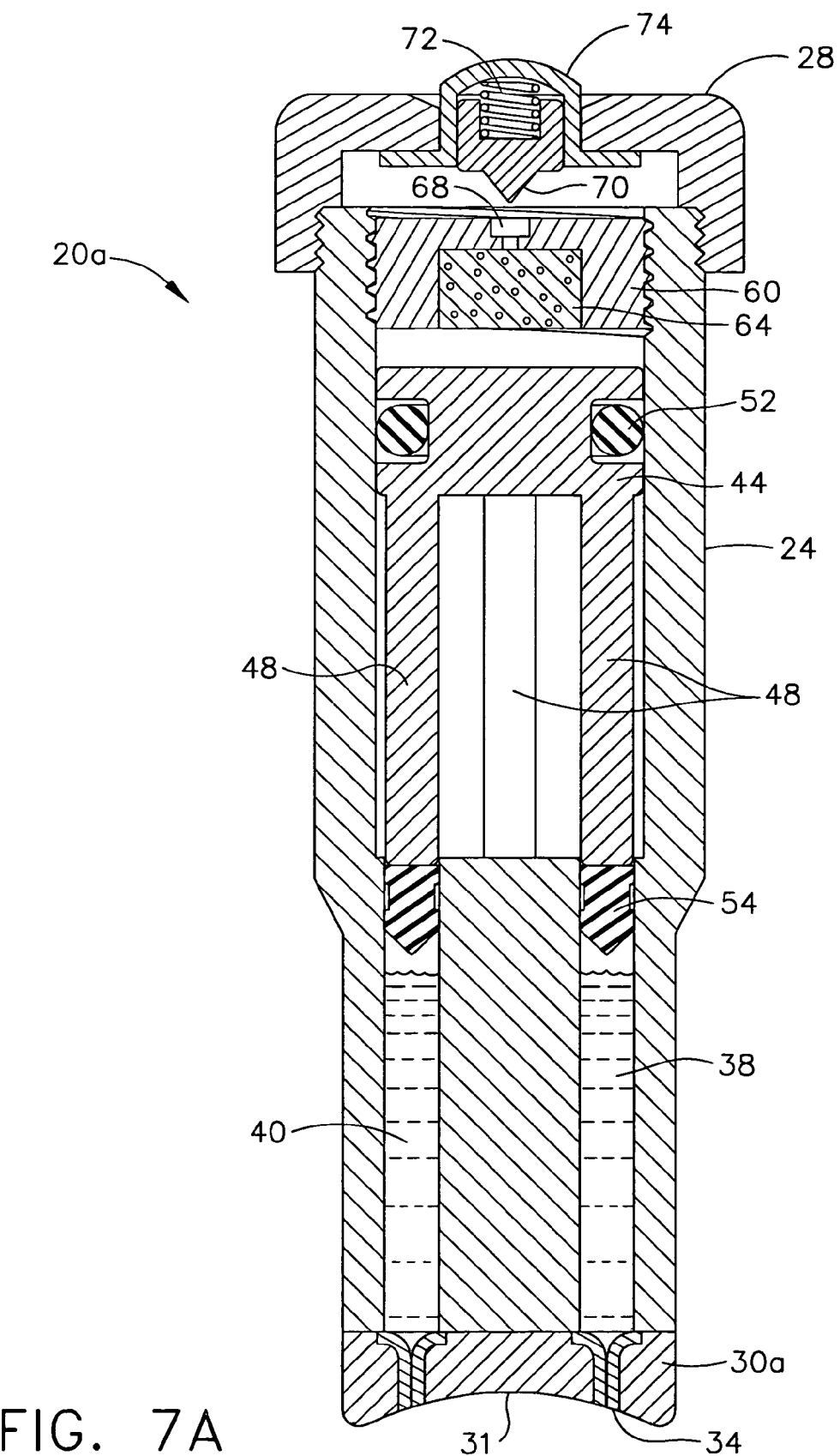
FIG. 7A is a view in cross-section of the device of FIG. 5 in accordance with the present invention.
Figure 7B:
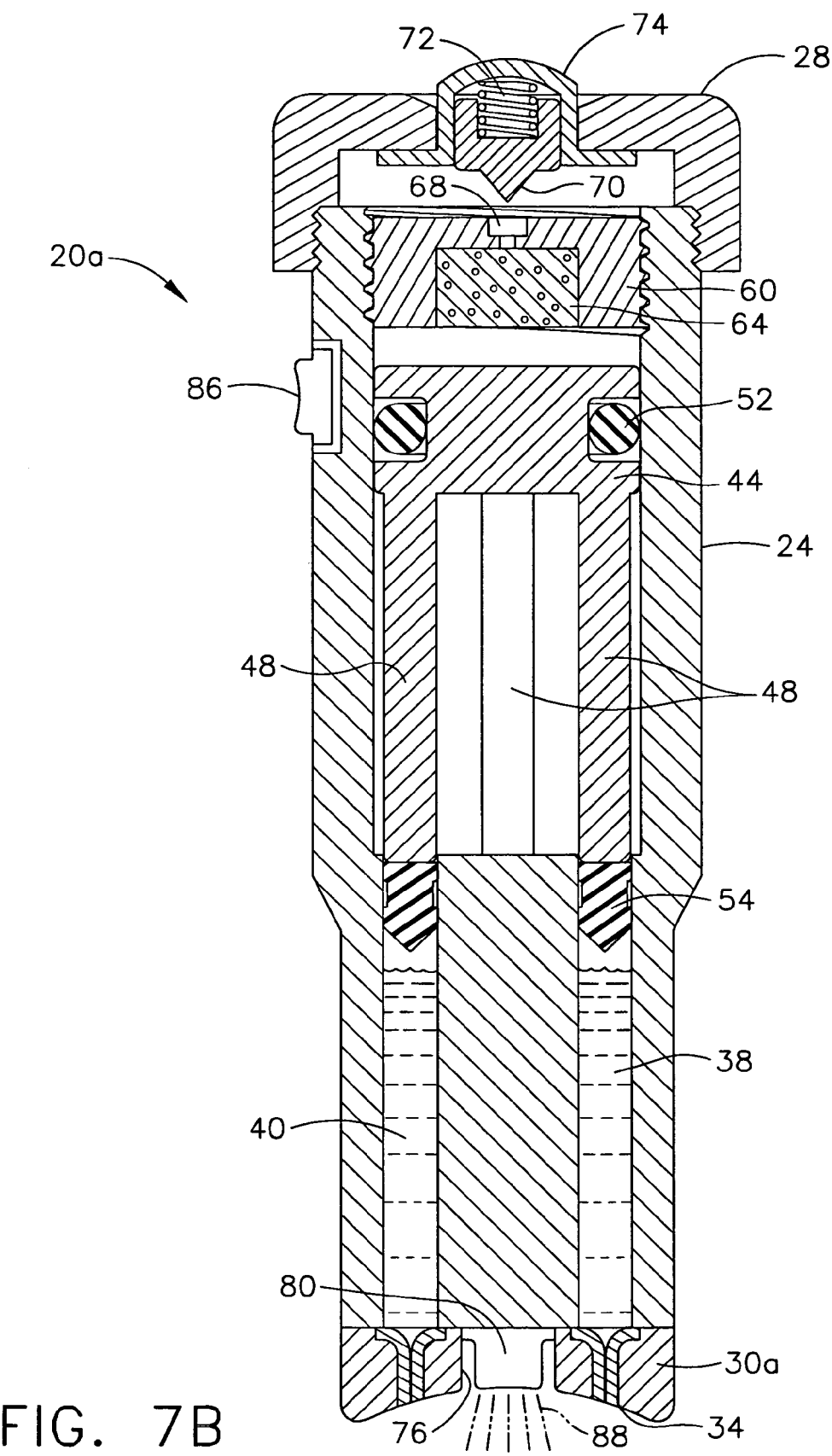
FIG. 7B is a view in cross-section of an alternative embodiment of the device of FIG. 7A having an LED focusing light in accordance with the present invention.

FIG. 7B depicts an alternative embodiment of drug delivery device 20a wherein a light emitting diode (LED) cavity 76 is provided at the center portion (open space) of the circumferential ring of the contoured distal end 31 of nozzle plate 30a. An LED 80 is positioned in the LED cavity 76 for dispersing a focusing light (focusing LED light) 88 under operational control from switch 86 movably positioned at an exterior portion of the housing 24 (in this example near the proximal end of housing 24). Switch 86 serves as a power switch for activating LED 80 to project focusing light 88, i.e. switch 86 serves as an "On", "Off" switch for the LED 80 and light 88. For sake of brevity, the contacts, leads and wires operatively connecting the LED 80 to the switch 86 are not shown, but are well understood and can be well appreciated by one having a level of ordinary skill in this field.

Focusing light 88 is used to attract the direct attention of the patient, align and focus the pupil of eye 100 and serves as a focal point of patient's attention in order to get the patient to mentally relax (basically distract the patient) while drug 40 is delivered to the eye 100 under microjet propulsion. Thus, LED 80 and focusing light 88 serves as a means for lowering the patient's stress levels and anxiety normally associated with receiving a drug injection, particularly, in such a sensitive area as the eye 100.

Alternatively, in lieu of an LED 80, an element or feature that is luminescent (including self-luminescent) or an element or feature having a luminescent coating, such as a dot having self-luminescent coating that is used as a focal point and can be used to attract the direct attention of the patient and focus of the pupil of eye 100 for serving as a focal point of patient's attention in order to get the patient to mentally relax in anticipation of and while receiving the injected drug 40 under microjet propulsion. A tritium-coated dot is one of these suitable substitutes as an example.

Figure 10:
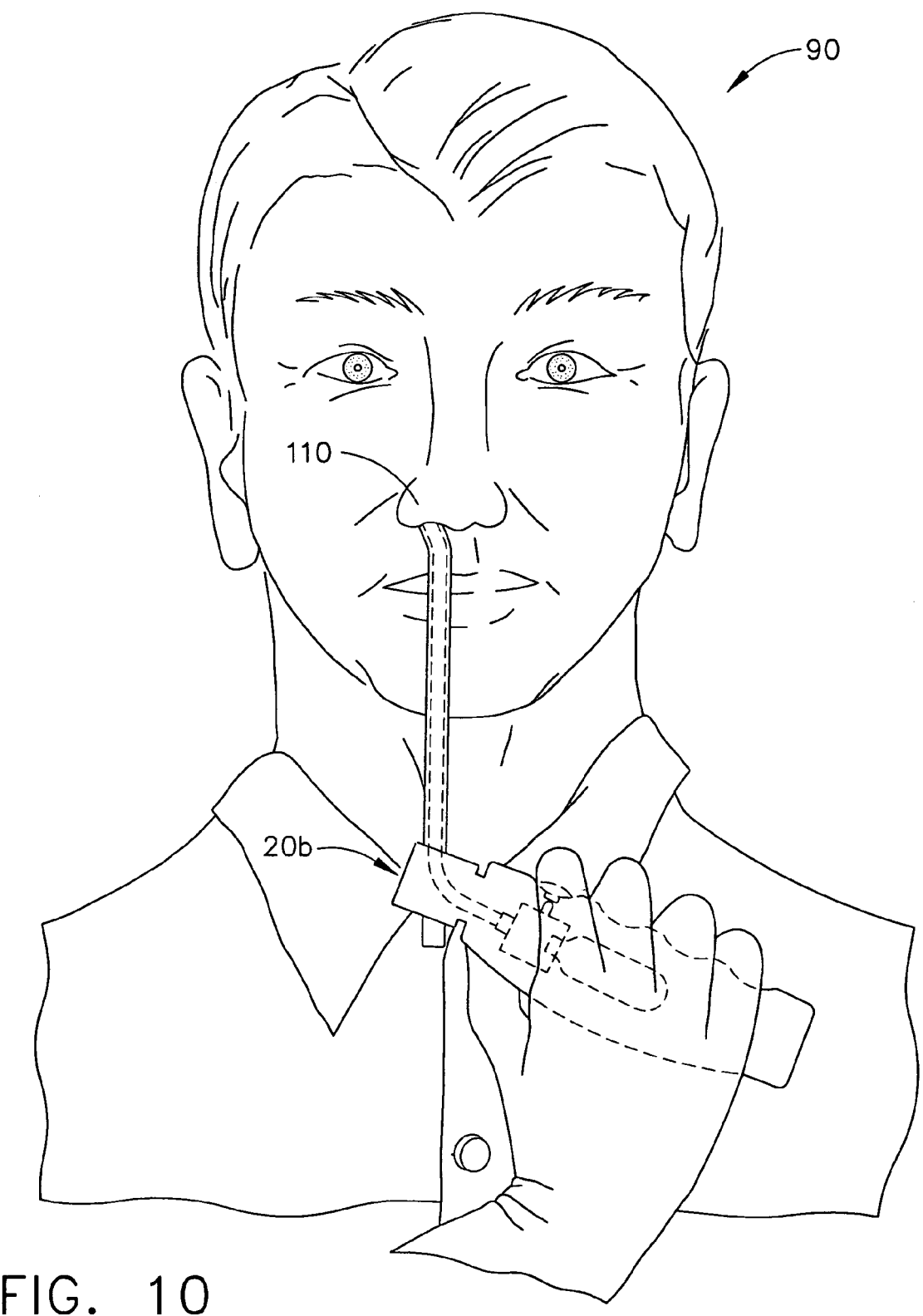
FIG. 10 is an illustration of the device in FIG. 8 in use for a nasal application in accordance with the present invention.

FIGS. 8, 9 and 10 illustrate another embodiment of the present invention wherein the drug delivery device 20b uses an elongated, cylindrical tube as a delivery tube 25 having a pressure chamber 27 therein. A handle 23 is connected to the delivery tube 25 at a proximal portion of the delivery tube 25. A valve 33 is connected to the proximal end of the delivery tube 25 and pressure chamber 27 and a source of compressed gas 36, such as compressed $CO_2$ gas contained in a cartridge 36 and is connected at another end of the valve 33 and contained within the handle 23. Cartridge 36 is a miniature compressed gas cylinder containing a compressed gas such as $CO_2$ with ability to achieve and delivery pressures as high as 2,000 psi. Valve 33 regulates the release of compressed gas from the cartridge 36 into the pressure chamber 27 of delivery tube 25 by activation button 74a located at a convenient location on the handle 23, for instance, easily accessible with the pad of the fore finger of patient or user's hand.

If desired, a detachably connected cover (not shown) can be used with handle 23 in order to provide direct access to the gas cartridge 36 for exchanging the cartridge 36 after expenditure of its contents (when empty) with a freshly charged (full) gas cartridge 36 thereby making the drug delivery device 20b a multiple use device or reusable device.

As shown in FIG. 9, nozzle plate 30 and nozzles 34 are located at the distal end of the delivery tube 25 and pressure chamber 27 and are arranged as outwardly extending protrusions from the outer surface of nozzle plate 30 for providing the user 90 with tactile feedback for the proper positioning and alignment of the injection nozzles 34 on a surface of the user's body tissue, for instance, on the tissue located within a nostril of the nose 110 (as shown in FIG. 10) or tissue located within the patient's mouth (bucal application), such as the gums or roof of the mouth, or a location within a patient's ear, etc. Thus, drug delivery device 20b is appropriate for delivering drug 40 to difficult areas to access of a patient's body due to the elongated and low profile design.

Drug reservoirs 38, drug 40, reservoir seals 54, pushrods 48, piston 44 and O-ring 52 are arranged and function in the same manner or similar fashion as described for the embodiments of FIGS. 1-7B, except that these features are located within the delivery tube 25 and pressure chamber 27 at the distal end of the delivery tube 25 and pressure chamber 27.

Pressure chamber 27 allows compressed gas to be released from the cartridge 36 and channels the gas from the handle 23 to the piston 44 along the entire length of the delivery tube 25 which provides the driving force necessary to slidably advance the piston 44 and the affixed pushrods 48 through the reservoirs 38 causing the pushrods 48 to expel by microjet propulsion the drug 40 out through the injection nozzles 34.

Drug delivery device 20 (FIGS. 1-4), 20a (FIGS. 5, 6, 7A and 7B) and 20b (FIGS. 8-10) are intended to be compact in design, for example, having outer surface dimensions measuring about 2.00" in length and 0.600" in diameter (for the embodiments of FIGS. 1-4 and FIGS. 5, 6, 7A and 7B respectively), and very light in weight, for example only weighing several ounces. Ergonomically, it may be desirable to increase the size or significantly change the geometry, but the underlying functionality remains exactly the same as that presented in these figures.

Alternatively, the energy source for discharging a driving force to the piston 44 is compressed gas, such as $CO_2$ as one example, releasably housed in a gas cartridge 36 (FIG. 8). Moreover, the energy source for discharging a driving force to the piston 44 can be any type of energy force so long as it is capable of delivering drug under microjet propulsion according to the requirements set forth below and later in this disclosure. For example, the energy source must discharge ample energy sufficient enough in order to drive main drive piston 44 and associated pushrods 48 at a driving pressure that ranges from about 800 to about 2,000 psi. In turn, the energy and force at the tips of microzzles micronozzles 34 ranges from about 4,000 to about 25,000 psi at each microzzle tip, and preferably at a range from about 8,000 to about 12,000 psi at each microzzle tip, and more preferably at about 10,000 psi at each microzzle tip.

The volume of drug 40 delivered under microjet propulsion by drug delivery device 20 (FIGS. 1-4), 20a (FIGS. 5, 6, 7A and 7B) and 20b (FIGS. 8-10), in accordance with present invention, is customizable, adjustable and variable in order to accommodate delivery of any type of drug, any tissue type, and any type of medical application. Total delivered drug volumes may be adjusted according a volume range that is from about 10 micro liters (μl) or less to about 1 milliliter (ml) or greater depending upon the configuration or design of the drug delivery device 20, 20a and 20b.

Further, the diameter of the injection nozzle(s) 34 are variable and range from about 10 (μm) to about 50 (μm) or greater, yielding exceptionally fine injection streams of drug 40 and minimizing the number of nerve receptors impacted by an injection thereby reducing trauma, pain and discomfort for the patient. One aspect of the novelty and uniqueness of drug delivery device 20 (FIGS. 1-4), 20a (FIGS. 5, 6, 7A and 7B) and 20b (FIGS. 8-10) in accordance with the present invention is its use of one or more discrete drug reservoirs 38 which serve as injection chambers wherein each reservoir contains drug 40 as a portion of the overall injection volume of total dosage for drug 40 as best shown in FIG. 3 (drug delivery device 20 shown in its pre-fired configuration prior to delivering drug 40). And, each reservoir 38 has its own dedicated injection nozzle 34 of extremely small diameter. For instance, the diameter of each nozzle 34 ranges from about 10 μm to about 50 microns μm or from about 0.0004" to about 0.002". Thus, drug delivery device 20 (FIGS. 1-4), 20a (FIGS. 5, 6, 7A and 7B) and 20b (FIGS. 8-10) in accordance with the present invention divides the total delivery volume for drug 40 into and across multiple, discrete reservoirs 38 (for those embodiments according to the present invention having more than one injection reservoir 38), and delivers each drug volume contained therein into the patient's tissue at higher velocities as best shown in FIG. 4 (drug delivery device 20 shown in fired configuration after delivering drug 40 under microjet propulsion) than those injection velocities achieved with the conventional jet injectors such as those jet injectors outlined previously.

Accordingly, one advantage associated with drug delivery device 20 (FIGS. 1-4), 20a (FIGS. 5, 6, 7A and 7B) and 20b (FIGS. 8-10) in accordance with the present invention is a dramatic decrease in the time required to inject drug 40 wherein this time can be as short as 40 milliseconds (msec.). Even for a requirement for the delivery of 0.5 cc (or 0.5 ml) injection of drug 40, the injection time achieved by drug delivery device 20 (FIGS. 1-4), 20a (FIGS. 5, 6, 7A and 7B) and 20b (FIGS. 8-10) ranges from about 10 msec. to about 200 msec. (and, in one example, ranges from about 40 msec. to about 100 msec. for about 0.5 ml of certain types of drugs). A further aspect of the present invention is that since the area of the jet stream decreases with the square of the diameter, there is nearly a 100-fold reduction in the area of the skin or tissue affected by injection with drug delivery device 20 (FIGS. 1-4), 20a (FIGS. 5, 6, 7A and 7B) and 20b (FIGS. 8-10) as compared to the known thinnest conventional hypodermic needle (ultra-fine insulin needle having a 31-gauge cannula with a diameter of 0.010").

In one embodiment according to the present invention, drug delivery device 20 (FIGS. 1-4), 20a (FIGS. 5, 6, 7A and 7B) and 20b (FIGS. 8-10) is a single-use pre-filled drug delivery device (designed for one time use as a disposable unit, i.e. one time, single patient use only) that requires no advance preparation or adjustment by the healthcare provider or the patient. Thus, drug delivery device 20 (FIGS. 1-4), 20a (FIGS. 5, 6, 7A and 7B) and 20b (FIGS. 8-10) is ready-to-use as manufactured and provided.

Alternatively, drug delivery device 20 (FIGS. 1-4), 20a (FIGS. 5, 6, 7A and 7B) and 20b (FIGS. 8-10) is also intended to be a re-usable unit (for example, the main housing 24, cap 28 with activation button 74 and delivery tube 25 and handle 23 with activation button 74a would be re-used and re-sterilized if required) with a single-use, disposable inner assembly that is either pre-filled or reloaded by the patient or healthcare provider prior to administration, inserted into the housing 24 or handle 23 and delivery tube 25 (for the drug delivery device 20b) and then removed and discarded after use. In this case, the disposable inner assembly comprises primer 68, pyrotechnic charge 64 (or compressed gas cylinder 36), drug reservoir pushrods 48, drug reservoirs 38, injection nozzles 34. The re-usable housing 24 and delivery tube 25 and handle 23 and other components such as the cap 28 and activation buttons 74 and 74a are made of an appropriate material such as metal or metal alloy capable of withstanding re-use and re-sterilization if needed.

Additionally, in all embodiments of the present invention, the injection nozzles 34 can be in the form of array of injection nozzles 34 (in any desired pattern on the nozzle plate 30 and 30a) that are configured out-of-plane or at different angles of trajectory, for example, in order to provide targeted convergence of the drug 40 to either a particular target point in tissue, i.e. a single target point in the tissue for receipt of the entire injected volume of drug 40 or a plurality of desired target points in tissue.

Optimization of Microjet Propulsion Drug Delivery and Method of Manufacture

Figure 11:
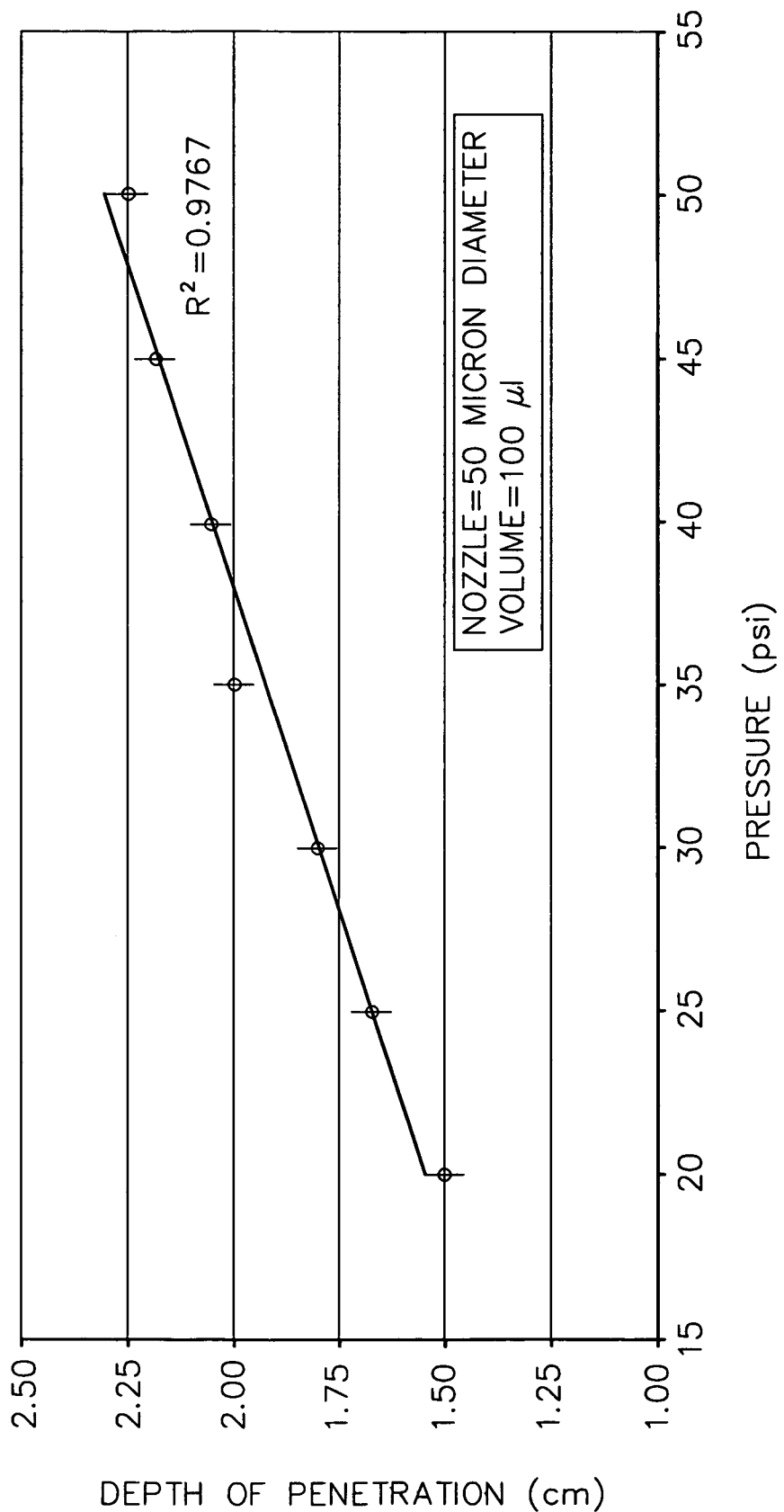
FIG. 11 is a graph depicting depth of penetration versus pressure study for the microjet drug delivery device having nozzle diameter of 50 μm and volume of drug delivered of 100 μl in accordance with the present invention.

There are two mechanisms that are used to characterize and measure the performance of the drug delivery device 20 (FIGS. 1-4), 20a (FIGS. 5, 6, 7A and 7B) and 20b (FIGS. 8-10) according to the present invention. The first mechanism is a predictive model based on the so-called Hagen-Pouiselle equation. This equation was used to estimate the affects of differing designs in the major elements and components of the drug delivery device 20 (FIGS. 1-4), 20a (FIGS. 5, 6, 7A and 7B) and 20b (FIGS. 8-10) and their methods of use and the resulting driving forces that are required to operate the drug delivery device in accordance with the performance criteria of the present invention. Additionally, the actual forces required to deliver requisite amounts of drug 40 under microjet propulsion were determined empirically through both in vitro and in vivo testing. For example, FIG. 11 is a graph representing the findings of one of these relevant in vitro studies used to determine depth of penetration versus pressure for the microjet drug delivery device (20, 20a and 20b) having nozzle diameter of 50 μm and volume of drug delivered of 100 μl in accordance with the present invention.

In development and manufacturing of the drug delivery device 20, 20a and 20b in accordance with the present invention, there is a force/volume/length trade-off based on the diameter of the individual drug reservoirs 38, as well as the diameters of the injection nozzles 34 and the desired injection velocity or mass flow rate of the expelled drug 40 or drug formulation 40. Further, the design of these components has implications for the duration of injection, the number of drug reservoirs 38 and injection nozzles 34 that are used, the size of the main piston 44 and even the physical properties needed by the materials of construction for many of the key elements of the drug delivery device 20, 20a and 20b.

This relationship is modeled by the Hagen-Pouiselle equation as follows:

$$F = 8Q\mu L(R^2/r^4)$$

where:
F=Injection force
Q=Flow rate of drug formulation or injectate
μ=viscosity of drug formulation or injectate
L=Length of injection nozzle
R=Radius of drug reservoir
r=radius of injection nozzle To demonstrate the usefulness of this equation, let's assume that it is desirable to deliver 500 micro liters (½ cc) of an aqueous drug formulation 40 (a drug solution 40 with viscosity μ=1 cps) to the subcutaneous layer of tissue at a flow rate Q of 5 cc/second. Further, let's assume that we are using an injection microjet or nozzle diameter of 50 microns (0.002"), or r=25 microns (0.001"). While we want to minimize the drug reservoir length, we also want to minimize the injection force. Thus, while shorter length is better, smaller diameter also means less force but a longer length. Thus, a convenient size is selected with respect to a reservoir length suitable to a hand-held microjet drug delivery device (20, 20a and 20b) while also attempting to minimize injection force. Consequently, 0.072" diameter drug reservoirs, or R=0.036" (0.914 mm) were selected. The length L of the injection nozzle 34 is determined by manufacturing constraints (a very small hole can only be made in a given material for a limited length). Accordingly, it is assumed that a suitable length L is 0.050" (1.27 mm). Thus, the Hagen-Pouiselle equation can estimate the injection force required for any given injection nozzle as follows:

With:
Q=5 cc/s
μ=1 cps
L=0.050"=0.127 cm
R=0.036"=0.091 cm
r=25 μm=0.0025 cm
$F = 8Q\mu L(R^2/r^4) = 10{,}218{,}121$ dynes or about 23 lbf.

The number of drug reservoirs 38 is determined by the total force the main drive piston 44 can exert divided by the force required to propel each of the drug reservoir pushrods 48 which act as individual pistons simultaneously in this example (expressed as a whole integer). The practical pressure achieved by either the pyrotechnic charge 64 or a compressed gas cylinder 36 is limited to about 2,000 psi. Consequently, given a main piston 44 diameter of 0.500" and the resulting area of $(0.250")^2$ times pi=0.196 square inches, the maximum driving force available is 2,000 psi×0.196 square inches or 392 pounds of force. With 23 pounds of force required to drive each drug reservoir pushrod 48 and 392 pounds of force available, the maximum number of drug reservoirs 38 that can be accommodated (as a whole integer) is 392 divided by 23 or a total of seventeen (17) reservoirs 38.

The length of each drug reservoir 38 is calculated as a result of the volume requirement for each. For purpose of example, assume that five (5) reservoirs are used. Thus, given that a total of 500 micro liters is required to be delivered through the five (5) reservoirs 38, each reservoir 38 will deliver 100 micro liters of drug 40. Given a reservoir diameter of 0.072" (1.83 mm), each reservoir length will be 100 micro liters divided by the reservoir area (pi×$(0.914 mm)^2$) or 38.1 mm long (1.50").

And, the injection flow rate Q has already been defined as 5 cc/s (as outlined above). Consequently, the total injection time is determined by the time required to inject the volume of drug 40 contained within each individual reservoir 38, which we have found to be 100 micro liters or $\frac{1}{10}^{th}$ of a cc. Thus, the injection time is 0.10 cc times the reciprocal of the flow rate Q or 20 milliseconds.

As a predictive model, the Hagen-Pouiselle equation is a useful tool for preliminary analysis and prediction of necessary design parameters for the elements of the drug delivery device 20, 20a and 20b, but as would be expected the empirical findings did differ from the predictive analysis. Both in vitro testing which included using a 2 mm thick ballistics gelatin over a saturated Pluronic (F127) solution and in vivo testing which including testing the drug delivery device in accordance with the present invention on the hairless guinea pig model had demonstrated that the drug formulation 40 is required to be pressurized to approximately 8,000 psi in order to achieve microjet propulsion, i.e. the velocities necessary for the drug formulation 40 to be delivered through the injection nozzles 34 to a depth of penetration in tissue, such as the skin, needed for therapeutic administration, i.e. in this case, subcutaneous administration.

Given, for example, that the drug reservoirs 38 have a diameter of 0.072", the cross-sectional area of each drug reservoir 38 is $(0.036)^2$ times pi or 0.004 square inches. With force F equal to pressure P times area A, the force needed to drive the pushrods 48 to achieve an 8,000 psi pressure in the drug formulation 40 is 8,000 times 0.004 or thirty-two (32) pounds of force. This was a modest increase over the 23 pounds of force predicted by Hagen-Pouiselle, but certainly along the same order of magnitude. Much of the increase is explained by the friction of the sliding reservoir seals 54 and O-ring 52.

Continuing with the values used in the example for the Hagen-Pouiselle equation, assuming that 500 micro liters of drug formulation 40 is required for the total administration and five (5) drug reservoirs 38 are being used for the design, then each reservoir 38 contains $^{500}/_5$ or 100 micro liters of drug formulation 40. With thirty-two (32) pounds of force needed for each drug reservoir 38 and the five drug reservoirs total, it was calculated that 32×5 or 160 pounds of total force is needed to drive all of the drug reservoir pushrods 48. Thus, the main drive piston 44 must exert a force of 160 pounds.

Given a diameter of 0.500" for the main drive piston 44 (note that this dimension may be higher or lower depending on the application and the practical ergonomic limitations of physical size), the area of the piston 44 is $(0.250")^2$ times pi or 0.196". Thus, the energy source must apply a pressure of F/A ($^{160}/_{.196}$) or 816 psi to the main drive piston 44. This pressure requirement is well within the performance specifications of either a pyrotechnic charge 64 or a miniature compressed gas source 36. The lengths of the drug reservoirs 38 and duration of injection will remain the same as those given in the Hagen-Pouiselle example.

The main drive piston assembly 44 acts as an accumulator for the pressure generated by the pyrotechnic charge 64 as shown in FIGS. 2, 3, 7A and 7B (or, alternatively, a compressed gas source 36 as shown in FIGS. 8 and 10), distributing the pressure and translating it as a driving force to the individual pushrods 48. The pushrods 48 are integral to the main drive piston 44, so the total load applied to the piston 44 is transferred proportionally to each of the pushrods 48. In the event that a larger size main piston diameter is required, this will translate to a larger exerted force for any given engine pressure. For example, if the main piston diameter is increased in our previous examples from 0.500" to 0.600", then the resulting force from a maximum engine pressure of 2,000 psi will increase from 2,000 psi×0.196 sq. in.=392 pounds of force to 2,000 psi×0.283 sq. in.=565 pounds of force. This increase in effective driving force permits the use of additional injection nozzles 34, which, in turn, reduces the volume in each nozzle 34, which, in turn, reduces the duration of the injection time, etc.

Finally, the nozzle geometry is determined by the desired diameter of the drug stream, the tensile/yield strength of the materials of construction, and the practical limitations of manufacturing a very small orifice at a cost effective economy of scale. While one goal of achieving a lightweight, compact hand-held drug delivery device 20, 20*a* and 20*b* with respect to nozzle geometry is "smaller is better", there are practical limits to constructing such nozzles 34.

In the known and conventional needle-free drug injectors, these known devices have a relatively large orifice (approximately 0.006"-0.008") because these are the practical limits of high volume injection molding in suitable thermoplastics (i.e., core pins smaller than this diameter are not practical at the high pressures and high shear required by injection molding in high volume production).

As noted for the drug delivery device 20, 20*a* and 20*b* in accordance with the present invention, the drug delivery device 20, 20*a* and 20*b* uses nozzles 34 in the 10 to 50 micron size and at significantly higher operating pressure than found with the known, conventional needle free jet injectors, such as those described previously above.

Consequently, drug delivery device 20, 20*a* and 20*b* in accordance with the present invention takes advantage of materials having high tensile and burst strength properties for the components of the drug delivery device 20, 20*a* and 20*b*. Such materials include ceramics, various metals and metal alloys, high strength engineering thermoplastics (such as PEEK™, Torlon™, Ultem™, etc.), and others. Thus, the present invention is also directed to using the most cost effective combination of such materials and to minimize part count, i.e. minimize the number of components and parts required.

Since the material used will need to withstand a given injection pressure in excess of 8,000 psi immediately at the nozzle tip, it is desirable to use discrete nozzles 34 fabricated in metal, metal alloy or ceramic (for instance, alumina or zirconia) and assemble to the housing 24 (FIGS. 1-7B) or delivery tube 25 (FIG. 8) by bonding or ultrasonic welding, for example. All of these materials can be formed by injection molding, although the final nozzle orifice would be secondarily formed using laser drilling, ultrasonic drilling, wire EDM machining, or the like. While not currently believed to be practical, developments in micro-injection molding may make molding of integral, fully finished injection nozzles entirely feasible and more cost effective than current approaches involving secondary finishing operations. Nonetheless, injection molding in high strength materials coupled with laser drilling to produce precise, repeatable injection nozzles 34 should satisfy engineering and cost requirements associated with the present invention.

In another example in accordance with the present invention, FIGS. 1-4 depict various views of the drug delivery device 20 that can be used to accelerate a multiplicity of small drug volumes 40 to a suitable velocity for delivery into tissue, for example, across the skin as part of a transdermal drug delivery procedure. Using this example to illustrate the function of the drug delivery device 20 under the assumption that the design of the drug delivery device 20 will require a total of thirty (30) injection nozzles 34 with each nozzle 34 having a diameter of 40 microns and a calculated drug volume of 3.3 µl per drug reservoir 38, or a total drug volume of 30×3.3=100 µl. Further, given a required velocity of 200 m/s for delivery of the drug 40, the force needed for each injection nozzle 34 can be calculated from the Hagen-Poiseuille equation yielding a value of approximately 10 lbs. per injection nozzle 34. Given thirty (30) injection nozzles 34, the total required loading force is 30×10=300 lbf. Assuming the main piston 44 surface area is 1 square inch, then 300 psi of pressure is needed to achieve the requisite performance parameters. Again, this performance criteria is achievable using the miniature compressed gas cylinder 36 (FIGS. 8 and 10) or the pyrotechnic charge 64 (FIGS. 2, 3, 7A and 7B). The advantage of the pyrotechnic charge is that the pressure profile can be controlled throughout the entire dispensing cycle, providing varying pressures at different times to optimize the drug dispensing. Moreover, as one can readily appreciate, a number of suitable energy sources may exist that can be used for the purpose of accelerating the drug 40 to the required velocities in order to achieve microjet propulsion criteria according to the present invention and the examples provided herein are in no way meant to limit the kind of energy source that may be used in the present invention.

As best illustrated in the graph depicted in FIG. 11, an in vitro study was conducted for the microjet drug delivery device (20, 20a and 20b) in accordance with the present invention in order to determine an optimal range for the depth of penetration (in cm) versus an optimal range of pressure (in psi). The nozzle 34 diameter was approximately 50 micron diameter wherein the volume of drug 40 delivered was approximately 100 µl. As clearly illustrated in FIG. 11, the delivery pressures for the microjet drug delivery device (20, 20a and 20b) can readily be adjusted to target any selected tissues. Thus, the microjet drug delivery device (20, 20a and 20b) is customizable in a manner that ensures that any particular drug can be delivered to a particular depth of penetration in a particular tissue type based on a particular delivery pressure according to the graph of FIG. 11. Accordingly, this customizable approach even allows for particular layers of tissue to be targeted for drug delivery. For example, the submucousal layer of tissue can be targeted exactly according to the algorithm depicted in FIG. 11.

Additionally, any number of drug reservoirs 38 and injection nozzles 34 can be utilized for the present invention (within practical limits). As demonstrated above, this can be anywhere from a single reservoir 38 and a single nozzle 34 to as many as fifty (50) or more reservoirs 38 and nozzles 34 respectively.

Standard semiconductor processes can readily fabricate the injection nozzles 34 similar to the fabrication of nozzles used in inkjet printing. Thus, injection nozzles 34 may be mass-produced silicon devices having an orifice diameter of between 3 and 10 microns as one example. The injection nozzles 34 can be fabricated as dense arrays on a silicon wafer and subsequently cut to the desired geometry. Wafer patterns, and therefore the array geometry, can be fabricated in any desired design. Consequently, the micronozzle array can be fabricated in any desired pattern such as a circular, elliptical, or semi-circular pattern, for example, and with any practical density of injection nozzles 34 that is required. Typically, every effort would be made to reduce the size of injection nozzles 34 and to maximize the number of injection nozzles 34 that such a wafer can yield.

Micro-molding of thermoplastics is an emerging technology that may also be useful for manufacturing the drug delivery device 20, 20a and 20b in accordance with the present invention. The advantages would be significant. While silicon wafers are planar structures, injection molded plastics are not. Thus, the array of injection nozzles 34 can be configured out-of-plane, for example, which would provide tremendous benefit in creating an array that is intended to be positioned with a targeted convergence. A further significant advantage is cost. A micronozzle array molded in a thermoplastic would cost pennies, in comparison to a silicon device that could easily range into dollars.

Other methods that may be used to construct the micronozzles 34, include micro-machining the orifices in place as part of the nozzle plate 30 or nozzle plate 30a having contoured distal end 31 (annular cup), machining or forming the orifices in glass, metal, ceramic, plastic, or other suitable material and then assembling (e.g., press fitting) into the contoured distal end 31 (annular cup), etc. Like the other major components of the drug delivery device 20, 20a and 20b in accordance with the present invention, the design or fabrication of the micronozzles 34 is not intended to be limited to a specific embodiment.

Thus, in general, the present invention is directed to a method for making or manufacturing a drug delivery device 20, 20a, and 20b in accordance with the present invention. Accordingly, this method comprises several key steps such as identifying a drug desired to be delivered (can be based on any desired treatment or diseases state or condition that is being targeted for treatment). Additionally, a volume of the drug desired to be delivered is also identified. Moreover, key parameters for features of the device 20, 20a and 20b are determined. This includes parameters such as the diameter for the one or more drug reservoirs 38 and diameter for the one or more injection nozzles 34 which are established in advance. Furthermore, a tissue model for the tissue type or disease to be treated is identified. For example, the tissue model is any appropriate in vitro or in vivo model acceptable for this purpose. Thus, the tissue model can be based on material, for example, tissue model that is synthetic, natural, mammal (to include any animal or human tissue), living tissue, preserved tissue, etc.

Additionally, other key steps include identifying a penetration depth in the tissue model for the delivery of the drug. This includes targeting any desired or particular layer of the tissue that is considered appropriate for microjet injection of the drug 40. And, the drug 40 is tested in the tissue model by injecting the drug 40 into the tissue model using the drug delivery device 20, 20a and 20b in accordance with the present invention under variable pressure until the desired penetration depth or desired tissue layer is achieved.

In using the method according to the present invention, an optimal pressure range is identified for the drug delivery device 20, 20a and 20b that achieves the desired penetration depth or desired tissue layer. As outlined previously above, an optimal pressure range has been identified to be ≤2,000 psi at main piston 44 and an optimal pressure range of ≤8,000 psi has been identified for the area at a tip of the injection nozzle 34.

The method according to the present invention also includes using predictive modeling for predicting the optimal pressure range required by determining the required injection force (F). Determining the injection force (F) is accomplished according to the formula: $F=8Q\mu L(R^2/r^4)$; where Q=flow rate of drug; μ=viscosity of drug; L=length of injection nozzle; R=radius of drug reservoir; and r=radius of injection nozzle.

Methods of Use

For transdermal or dermal delivery, the drug delivery device 20 (FIGS. 1-4) is in its pre-fired configuration and loaded with the total volume of drug 40 to be delivered wherein drug delivery device 20 is placed firmly against and perpendicular to any desired site of injection (typically the back of the arm, the stomach or the thigh) with the skin pinched in a conventional manner. Since the injection nozzles 34 terminate as small outward protrusions from the outer surface of nozzle plate 30, the user is provided with instant tactile feedback for the proper positioning and alignment of the injection nozzles 34 on the surface of the user's body tissue at the desired site of injection.

As best shown in FIG. 4, upon depressing the activation button 74, striker pin 70 strikes primer 68 thereby activating primer 68, which, in turn, cause the extremely rapid combustion of pyrotechnic charge 64. This controlled explosion provides the driving force necessary to slidably advance the piston 44 and the affixed pushrods 48 through the reservoirs 38 causing the pushrods 48 to expel by microjet propulsion the drug 40 out through the injection nozzles 34.

Although this example described immediately above is directed to subcutaneous or cutaneous delivery, there are other examples for the drug delivery device 20a and 20b that are used in applications such as intra-ocular (drug delivery device 20a), intra-oral (drug delivery device 20b), intra-nasal (drug delivery device 20b), intra-aural (drug delivery device 20b), and, more broadly, intra-mucosal delivery in general (drug delivery devices 20, 20a and 20b). It should be also noted that "transdermal" delivery is intended to mean all forms of delivery such as: intradermal, subcutaneous, and intramuscular.

In another embodiment according to the present invention, the drug delivery device 20a (FIGS. 5, 6, 7A and 7B) is particularly well suited for ocular use and can deliver any drug 40 needed for intra-ocular micro-injection (especially intra-scleral or intra-vitreal injections). Such drugs known for these particular applications include VEGF antagonists, corticosteroids, and anti-angiogenic drugs in general. Indications treated by the drug delivery device 20a (FIGS. 5, 6, 7A and 7B) in accordance with the present invention include, for example, diabetic retinopathy, macular degeneration and other diseases involving neovascularization in the eye.

In this embodiment, contoured distal end or cup 31 is placed over or on the surface of the eye 100 with the open center portion of cup 31 overlaying the cornea. The micronozzles or injection nozzles 34 are spaced and configured about the concentric ring of contoured distal end 31 such that they are in contact with the sclera. In one embodiment in accordance with the present invention, the injection nozzles 34 are configured in a circular or elliptical pattern. However, it is contemplated by the present invention that the injection nozzles 34 be arranged or configured in any desired configuration or pattern.

Upon depression of activation button 74, the injection stream of drug 40, as shown in FIG. 5, penetrates deep into the eye 100 through the sclera, and into the aqueous humor or the vitreous or any other desired tissue layer of portion of eye 100. Preferably the injected drug 40 under microjet propulsion is targeted toward the back of the eye 100 as presently depicted. As mentioned previously, currently, many of the drugs of interest are administered by injecting directly into the eye with a conventional needle and syringe. As can be greatly appreciated, this is a somewhat risky procedure and requires that the injection be administered by a trained ophthalmologist. There are significant risks to the patient associated with these conventional techniques and include retinal detachment, scarring after repeated injections, and even blindness. Further, the injection itself is dismaying to the patient and requires that the patient be very still during the several seconds of the injection itself.

In the present invention, injection of the drug 40 into the eye 100 is extremely rapid. For example, given a stream velocity of the injected drug 40 under microjet propulsion of 100 m/s for a drug reservoir 38 having a volume of 20 micro liters, the entire injection only requires about 10 milliseconds using drug delivery device 20a in accordance with the present invention. Assuming that the patient were to intentionally move his or her eyes 100 from one side to the other during the injection, and assuming eye movement occurs at a rate of about 1 cm/s, the eye could only travel about $\frac{1}{10}^{th}$ of a millimeter in this period of time, a distance of no consequence when using drug delivery device 20a in accordance with the present invention. Consequently, this invention also represents a safer, more comfortable means of administering drugs to the eye 100 for both the physician and patient.

As contemplated by the present invention, drug delivery device 20a (FIGS. 5, 6, 7A and 7B) in accordance with the present invention offers a number of advantages over the conventional technology and techniques. For instance, the injection nozzles 34 can be designed to "aim" the injection stream at specific areas in the eye 100 (e.g., the back of the eye 100). Additionally, the depth of penetration of the drug 40 can be controlled without relying on the skill of the caregiver. Moreover, the risk of injury to the eye 100 is minimized with drug delivery device 20a (FIGS. 5, 6, 7A and 7B) in accordance with the present invention by minimizing the energy and tearing (trauma) to which the eye 100 is subjected due to the extremely rapid nature of the microjet propulsion of the drug into the tissue of the eye 100 (estimated to be as fast as about 10 milliseconds for injection of small doses of drug 40).

Moreover, the drug delivery device 20a has the ability to modulate the jet injection energy and injection stream geometry as a means to control the depth of delivery of the drug into the eye. Also, the design of the micronozzle geometry allows for the control the stream diameter, trajectory, cohesion, and focus. Additionally, the flexibility in the design of the micronozzle array allows for optimization of the drug delivery profile for any given drug, disease, or site of disease within the eye. Furthermore, the drug delivery device 20a provides an extremely rapid means of administering drug 40 to the eye 100 such that eye movement does not present an element of risk.

Additionally, many drugs 40 currently under pre-clinical and/or clinical investigation are potent drugs and require only periodic administration of small doses to the eye 100. Drug delivery device 20a (FIGS. 5, 6, 7A and 7B) in accordance with the present invention offers a more controlled, repeatable, safe, and comfortable means of delivering these drugs 40 to the eye 100 over any known devices and techniques available to date.

Another embodiment in accordance with the present invention is an intra-nasal application depicted in FIG. 10. Accordingly, the drug delivery device 20b (FIGS. 8-10) has particularly useful application in administering CNS (central nervous system) drugs 40 via microjet injection to the olfactory bulb of the nose 110 of the patient 90.

In this embodiment, drug delivery device 20b (FIGS. 8-10) is used to provide direct injection of drug 40 under microjet propulsion into the submucousal space of the nose 110 to the CSF of the olfactory lobe. For this purpose, doses of drug 40 of 20 mg or greater can be injected extremely rapidly (<50 milliseconds) into the submucousal space and the depth of injection can be precisely controlled such that the drug 40 is delivered precisely to this area without any harm of penetrating to an undesired location.

In another embodiment according to the present invention, drug delivery device 20b is also used for the intra-oral delivery of drug 40 wherein the drug can be microinjected into any desired area in the mouth such as intra-mucosal for such applications as treating tumors, i.e. targeted delivery of drug 40 under microjet propulsion aimed at treating a tumor, for example.

In yet another embodiment according to the present invention, drug delivery device 20b is used for the intra-aural delivery of drug 40 such that drug 40 can be microinjected into any desired portion of the ear or auditory canal for treating various diseases and conditions of the ear or those conditions that affect hearing, for example.

Additionally, in other embodiments according to the present invention, drug delivery device 20b is also useful for areas of the body that are difficult to access such as various canals, passageways, cavities or difficult surfaces to reach. Extended delivery tube 25 facilitates easy access to these injection sites for the injection of drug 40 under microjet propulsion to these difficult areas.

Thus, as described above the drug delivery device 20, 20a and 20b in accordance with the present invention has many novel features and advantages. Some of these novel features and advantages are summarized here for convenience such as extremely small injection nozzles (0.002" or smaller); multiple injection reservoirs and injection nozzles minimizing each volume of injection and injection time resulting in less pain; customizable, variable pressure injections to include high pressure injection to reach deep tissues and lower pressure to target more shallow tissues; ability to concentrate drug dose into a confined area or spread it out over a larger surface area; high volume injections divided into a small volume, discrete injectors (can achieve injection volumes equivalent to or larger than conventional jet injectors at more rapid delivery times; multiple medical applications (i.e., transdermal, intra-ocular, intranasal, intrabucal, etc.); efficient operation to include total energy requirements equivalent to those total energy requirements available with the prior art devices, but with the present invention being much faster in administering the drug and much less painful injection for the patient; ability to deliver multiple drugs (i.e., different drugs can be housed in different drug reservoirs which is something not possible with the known drug delivery devices currently available); and ability to separate excipients during storage until time of injection which improves long term stability of the drug 40.

There is no known or existing technology that provides the advantages afforded by the present invention, including safety, ease of use, precision in both dose and depth of penetration, patient comfort and acceptance. Other advantages associated with the present invention is that it can provide for the precise, targeted delivery of small molecules and large molecules alike to include macromolecules such as large proteins, cells or other biological molecules and drugs. And, another advantage is that the microjet drug delivery device in accordance with the present invention is extremely rapid in its delivery of the drug, i.e. about ≤10 ms delivery resulting in nearly pain free injection.

The present invention contemplates that a significant reduction in the nozzle orifice size will result in reduced pain to the patient. Further, the present invention enables practical new uses of jet injection technology such as transmucosal delivery.

It is an advantage of the present invention that a plurality of nozzles may be employed, arranged in an array and having space between each adjacent nozzle, defining a two-dimensional planar structure that can lie flat on the skin and, thus, ensure perpendicularity.

Moreover, the present invention provides for true needle-free delivery of drugs regardless of size of the drug molecules involved as well as provide for true needle-free delivery of drugs with minimal trauma to tissue and that are suitable for delivering drugs in sensitive areas of the body such as the eye, nasal passageways, mouth, etc.

And, the drug delivery device 20, 20a and 20b are simple and efficient in design and construction, low cost and easy to manufacture. Accordingly, the microjet drug delivery device in accordance with the present invention has an appropriate design that is extremely suitable for a single patient use only disposable device if desired.

Inasmuch as the foregoing specification comprises preferred embodiments of the invention, it is understood that variations and modifications may be made herein, in accordance with the inventive principles disclosed, without departing from the scope of the invention.

While preferred embodiments of the present invention have been shown and described herein, it will be obvious to those skilled in the art that such embodiments are provided by way of example only. Numerous variations, changes and substitutions will now occur to those skilled in the art without departing from the invention. Accordingly, it is intended that the invention be limited only by the spirit and scope of the appended claims.

What is claimed is:

1. A method for delivering a drug into tissue comprising the steps of:
   providing a drug delivery device having at least one nozzle and a drug contained in a portion of the device;
   identifying a site for delivery of the drug in the eye;
   placing a portion of the device on or near the site; and
   delivering the drug as a fine stream into the tissue at the site through the at least one nozzle of the device under needle-free microjet propulsion at a driving pressure from about 800 to about 2,000 psi such that the pressure of the drug leaving the nozzle is from about 4,000 to about 25,000 psi.

2. The method according to claim 1, further comprising using the device to treat diabetic retinopathy.

3. The method according to claim 1, further comprising using the device to treat macular degeneration.

4. The method according to claim 1, further comprising using the device to treat neovascularization of the eye.

5. The method according to claim 1, further comprising placing the portion of the device on or near a cavity and delivering the drug into the cavity.

6. The method of claim 1 wherein the drug is delivered to an area of the eye outside of the pupil.

7. The method of claim 1 wherein the drug is delivered to the sclera.

8. The method of claim 1 wherein the drug is delivered to the vitreous.

* * * * *